(12) United States Patent
Lee et al.

(10) Patent No.: US 7,585,573 B2
(45) Date of Patent: Sep. 8, 2009

(54) IR COMPOUND AND ORGANIC ELECTROLUMINESCENT DEVICE USING THE SAME

(75) Inventors: Seok-Jong Lee, Suwon-si (KR);
Seung-Gak Yang, Suwon-si (KR);
Hee-Yeon Kim, Suwon-si (KR);
Young-Kook Kim, Suwon-si (KR);
Seok-Hwan Hwang, Suwon-si (KR);
Dae-Yup Shin, Suwon-si (KR);
Young-Rag Do, Seoul (KR);
Dong-Hyun Jung, Suwon-si (KR)

(73) Assignee: Samsung Mobile Display Co., Ltd., Yongin (KR)

( * ) Notice: Subject to any disclaimer, the term of this patent is extended or adjusted under 35 U.S.C. 154(b) by 649 days.

(21) Appl. No.: 11/046,758

(22) Filed: Feb. 1, 2005

(65) Prior Publication Data
US 2005/0170209 A1  Aug. 4, 2005

(30) Foreign Application Priority Data
Feb. 2, 2004 (KR) .................. 10-2004-0006592

(51) Int. Cl.
*H01L 51/54* (2006.01)
*C09K 11/06* (2006.01)

(52) U.S. Cl. .................. 428/690; 546/4; 313/504; 313/506; 252/301.16; 257/102; 257/E51.044; 428/917

(58) Field of Classification Search .................. 546/4, 546/6, 7, 10; 257/40, E51.02, E51.041, E51.044; 525/281; 544/225
See application file for complete search history.

(56) References Cited

U.S. PATENT DOCUMENTS

2001/0019782 A1* 9/2001 Igarashi et al. .............. 428/690
2002/0024293 A1* 2/2002 Igarashi et al. .............. 313/483
2002/0034656 A1* 3/2002 Thompson et al. .......... 428/690

FOREIGN PATENT DOCUMENTS

JP       2001247859         9/2001

OTHER PUBLICATIONS

Highly Phosphorescent Bis-Cyclometalated Iridium Complexes: Synthesis, Photophysical Characterization, and Use in Organic Light Emitting Diodes; Sergey Lamansky, et al.; J. Am. Chem. Soc.; 2001, vol. 123, pp. 4304-4312.
Synthesis and Characterization of Phosphorescent Cyclometalated Iridium Complexes; Sergey Lamansky, et al.; Inorg. Chem., 2001; vol. 40, pp. 1704-1711.
New Efficient Electroluminescent Materials Based on Organometallic Ir Complexes; Vladimir V. Grushin, et al.; Chem. Commun., 2001; pp. 1494-1495.
Endothermic Energy Transfer: a Mechanism for Generating Very Efficient High-Energy Phosphorescent Emission in Organic Materials; Chihaya Adachi, et al.; Applied Physics Letter; vol. 79, No. 13; pp. 2082-2084.
19.5L: Late-News Paper: Inkjet-Printed Bus and Address Electrodes for Plasma Display; M. Furusawa, et al.; SID 02 Digest; 2002; pp. 753-755.
Chinese Office Action dated Mar. 28, 2008.

* cited by examiner

*Primary Examiner*—D. Lawrence Tarazano
*Assistant Examiner*—Michael Wilson
(74) *Attorney, Agent, or Firm*—H.C. Park & Associates, PLC

(57) ABSTRACT

An Ir compound can be a blue phosphorescent material. An organic electroluminescent device can use such a material. An organic layer, such as a light emitting layer, can be composed of the Ir compound. An organic electroluminescent device including such an organic layer may exhibit high color purity and emits dark blue light. Such an organic electroluminescent device may have low consumption power.

10 Claims, 12 Drawing Sheets

IR COMPOUND AND ORGANIC ELECTROLUMINESCENT DEVICE USING THE SAME

BACKGROUND OF THE INVENTION

This application claims the benefit of Korean patent Application No. 10-2004-0006592, filed on Feb. 2, 2004, which is incorporated herein in its entirety by reference.

1. Field of the Invention

The present invention relates to an Ir compound and an organic electroluminescent device using the same, and more particularly, an Ir-containing organic metal based blue phosphorescent compound for an organic electroluminescent device, a method of manufacturing the same, and an organic electroluminescent device using the Ir compound.

2. Description of the Related Art

In a conventional organic electroluminescent (EL) device, an anode is formed on a substrate. A hole transporting layer, a light emitting layer, an electron transporting layer, and a cathode are sequentially deposited on the anode. The hole transporting layer, the light emitting layer, and the electron transporting layer are each made from an organic compound.

When a voltage is applied to the anode and the cathode, holes from the anode migrate toward the emission layer via the hole transport layer. Electrons from the cathode are injected into the light-emitting layer via the electron transport layer. Thereafter, the electrons and the holes recombine with each other at the emission layer to generate excitons. When the excitons are converted from an excited state to a ground state, a fluorescent molecule of the emission layer emits light, which displays an image. Light emission through conversion from a single excited state (S1) to a ground state (SO) is fluorescence, and light emission through conversion from a triplet excited state (T1) to a ground state (SO) is phosphorescence.

With respect to fluorescence, the proportion of singlet excited state is 25% (the proportion of triplet excited state is 75), and thus, there is a limitation on light emission efficiency. On the other hand, with respect to phosphorescence, the proportion of the triplet excited state and the singlet excited state may be 75% and 25%, respectively. Therefore, a theoretical internal quantum efficiency may reach 100%.

Light-emitting materials using T1 are being developed. For example, Princeton University and South California University have presented phosphorescent materials using an Ir compound and a platinum compound [Sergey Lamansky et al. *Inorg. Chem.*, 40, 1704-1711, 2001 and *J. Am. Chem. Soc.*, 123, 4304-4312, 2001]. Similarly, (4,6-F2ppy)2Irpic [Chihaya Adachi et al. *Appl. Phys. Lett.*, 79, 2082-2084, 2001] and an Ir compound with a fluorinated ppy ligand [Vladimir V. Grushin etc. *Chem. Commun.*, 1494-1495, 2001] have been introduced as a blue light-emitting material. However, (4,6-F2ppy) 2Irpic emits light with a blue sky region. Additionally, the shoulder peak of (4,6-F2ppy)2Irpic is large, thereby increasing the y value of color purity in the NTSC chromaticity diagram. Until now, a proper host material has not been developed for blue light emitting material. As a result, blue light emitting material has low efficiency and short lifetime compared to red and green phosphorescent materials. Therefore, a blue light emitting material with dark blue light emitting characteristics, high efficiency, and long lifetime, is needed.

SUMMARY OF THE INVENTION

The present invention provides a dark blue phosphorescent compound having high color purity and low power consumption.

The present invention also provides an organic electroluminescent device using a blue phosphorescent compound as a coloring substance or a dopant material.

The present invention provides an Ir compound represented by formula 1:

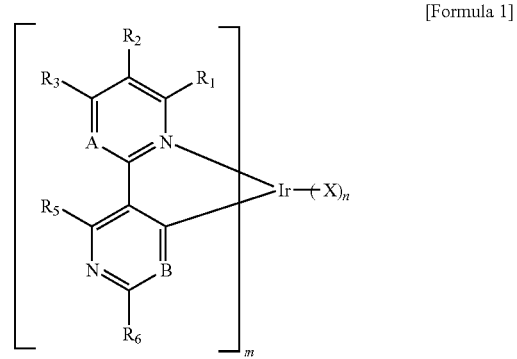

[Formula 1]

where A may be either $—C(R_4)—$ or $—N—$; B may be either $—C(R_7)—$ or $—N—$; $R_1, R_2, R_3, R_4, R_5, R_6$, and $R_7$ may each independently be H, a cyano group, a hydroxyl group, a nitro group, a halogen atom, a substituted or unsubstituted C1-C20 alkyl group, a substituted or unsubstituted C1-C20 alkoxy group, a substituted or unsubstituted C6-C20 aryl group, a substituted or unsubstituted C7-C20 arylalkyl group, a substituted or unsubstituted C2-C20 alkylalkoxy group, a substituted or unsubstituted C7-C20 arylalkoxy group, a substituted or unsubstituted C6-C20 arylamino group, a substituted or unsubstituted C1-C20 alkylamino group, or a substituted or unsubstituted C2-C20 heterocyclic group; at least two substituents selected from $R_1, R_2, R_3$, and $R_4$, $R_4$ $R_5$, and $R_4$ and $R_6$ may be connected to one another to form a saturated or unsaturated carbon ring, or a saturated or unsaturated hetero ring; X may be a monoanionic bidentate ligand; m may be either 2 or 3; n may be either 0 or 1; and the sum of m and n may equal 3.

The present invention also provides an organic electroluminescent device including an organic film interposed between a pair of electrodes. The organic film may be composed of an Ir compound.

DETAILED DESCRIPTION OF THE INVENTION

Figure 1:
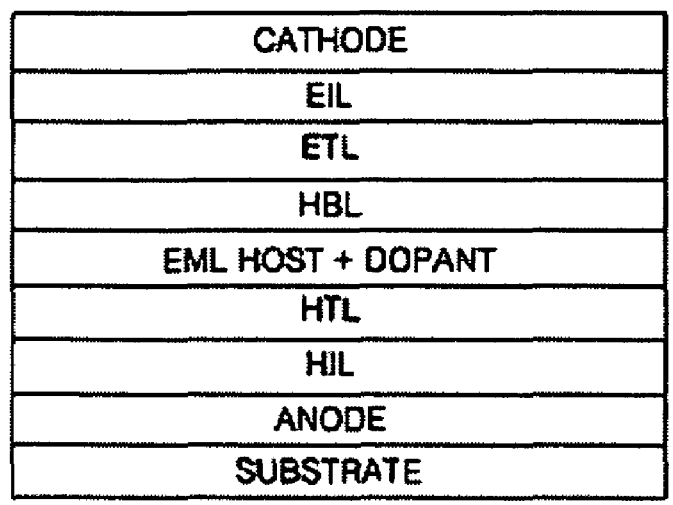
FIG. 1 is a sectional view illustrating the schematic structure of a conventional organic electroluminescent device.
Figure 2:
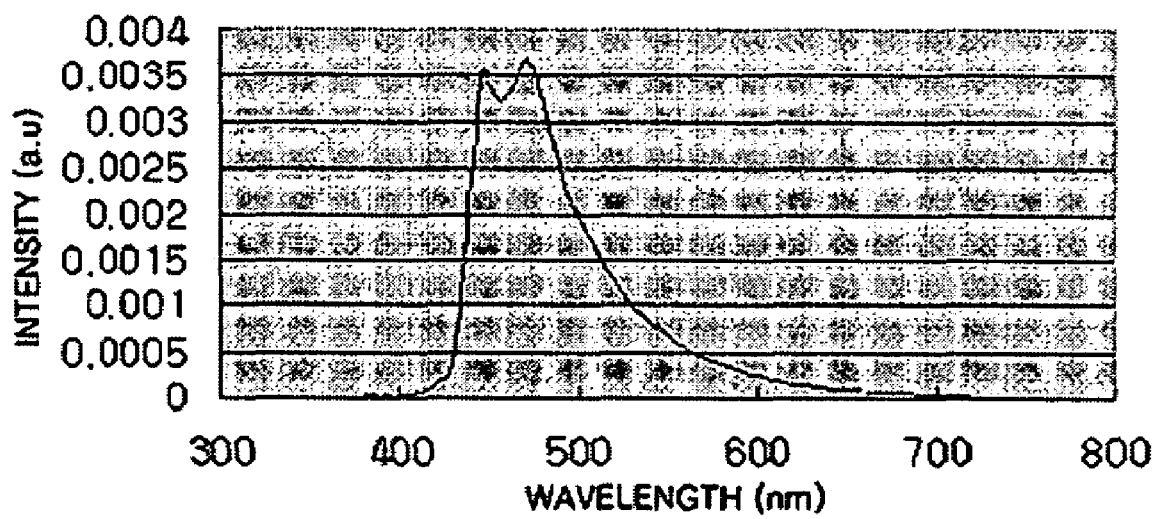
FIGS. 2, 7, 12, and 17 illustrate the electroluminescence (EL) spectra of organic electroluminescent devices according to Examples 1-4, respectively.
Figure 3:
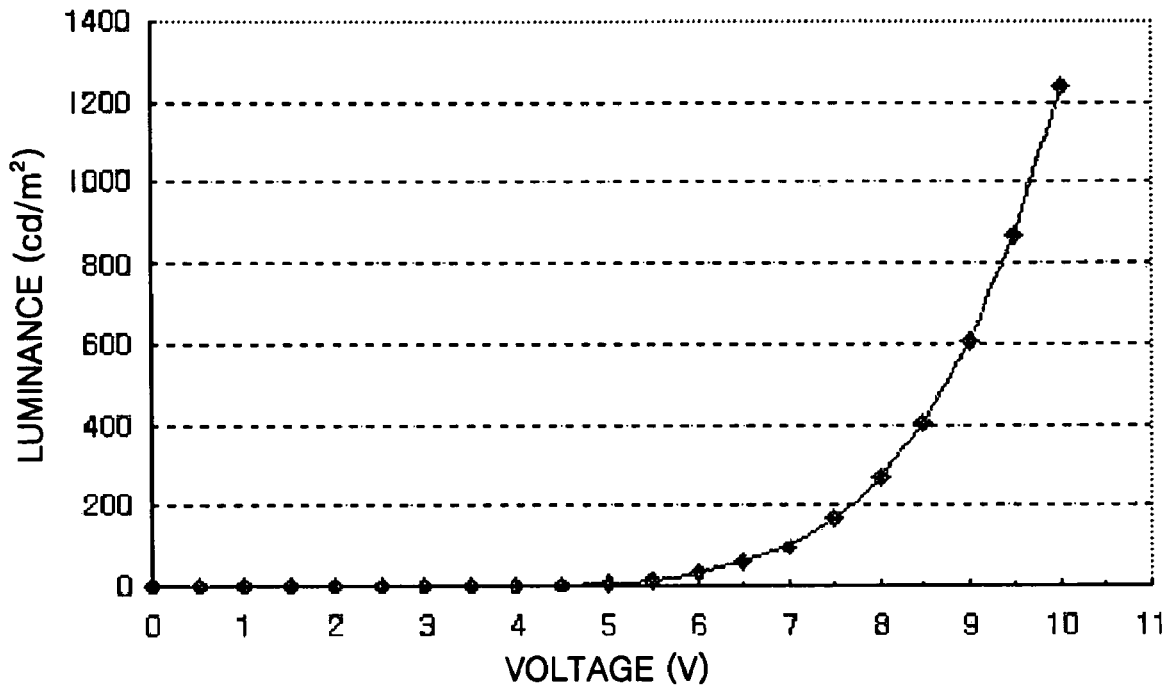
FIGS. 3, 8, 13, and 18 are graphs illustrating luminance with respect to a voltage of the organic electroluminescent devices according to Examples 1-4, respectively.
Figure 4:
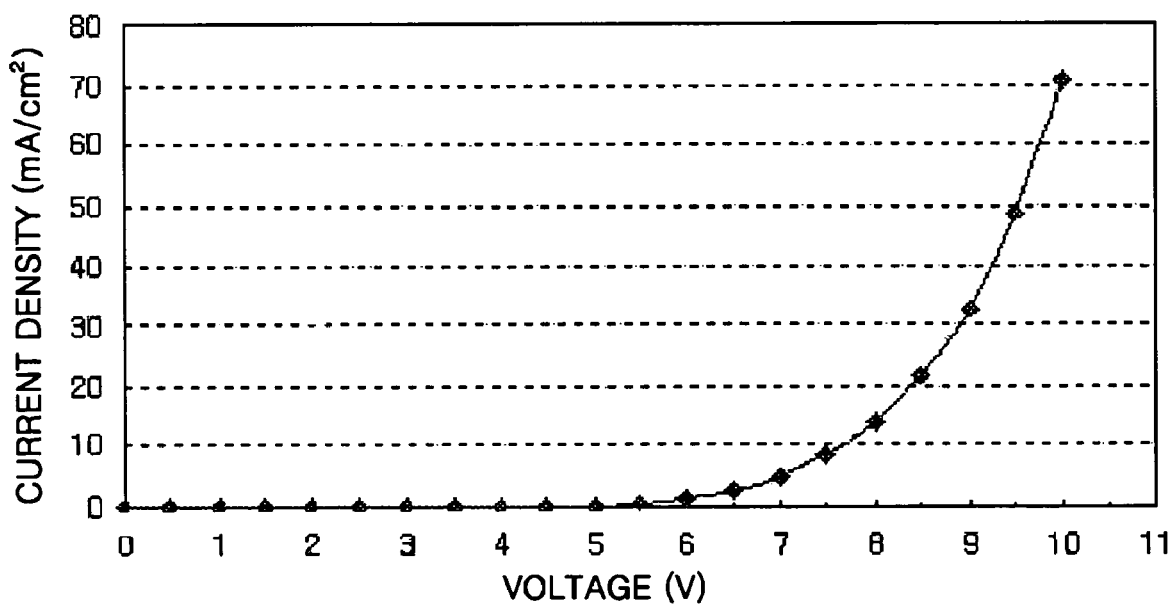
FIGS. 4, 9, 14, and 19 are graphs illustrating current density with respect to a voltage of the organic electroluminescent devices according to Examples 1-4, respectively.
Figure 5:
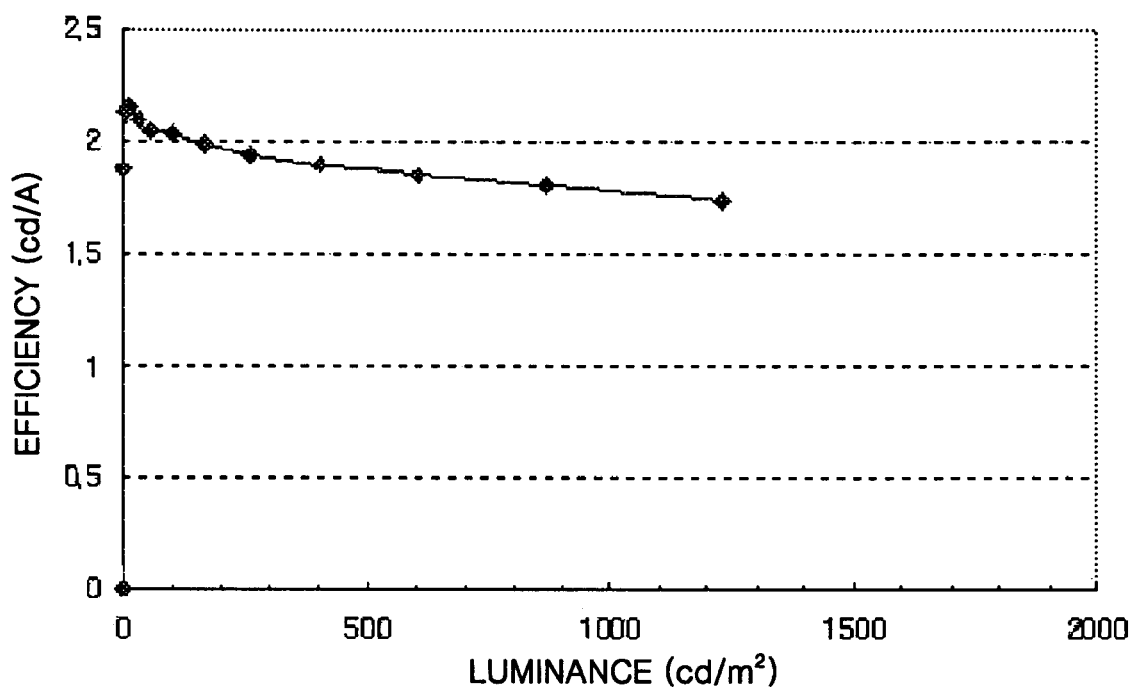
FIGS. 5, 10, 15, and 20 are graphs illustrating current efficiency with respect to the luminance of the organic electroluminescent devices according to Examples 1-4, respectively.

The present invention provides, for example, an Ir compound represented by formula 1. The Ir compound can be of the form represented by, for example, formulas 2 or 3 depending on the combination of m and n.

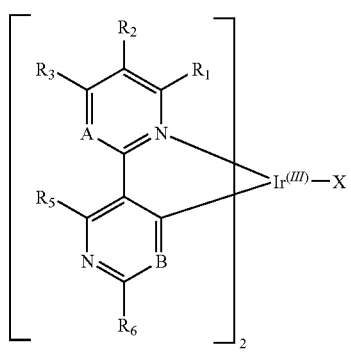

[Formula 2]

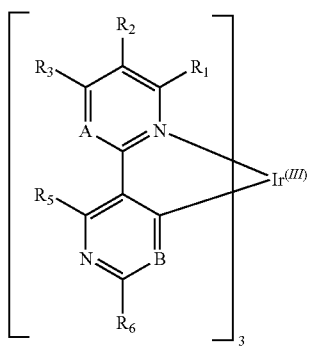

[Formula 3]

in which A, B, $R_1$-$R_6$ and X may be the same as described in formula 1.

In formulas 1-3, X is a monoanionic bidentate ligand such as acetylacetonate (acac), hexafluoroacetylacetonate (hfacac), picolinate (pic), salicylanilide (sal), quinolinecarboxylate (quin), 8-hydroxyquinolinate (hquin), L-proline (L-pro), 1,5-dimethyl-3-pyrazole carboxylate (dm3pc), imineacetylacetonate (imineacac), dibenzoylmethane (dbm), tetrametyl heptandionate (tmd), 1-(2-hydroxyphenyl) pyrazolate (oppz), or phenylpyrazole (ppz). The forgoing compounds may be represented by formula 4:

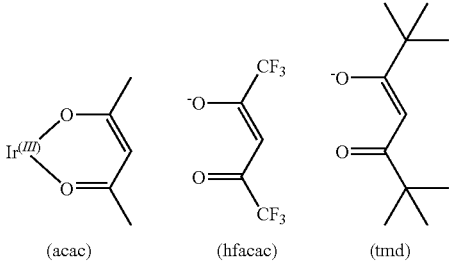

[Formula 4]

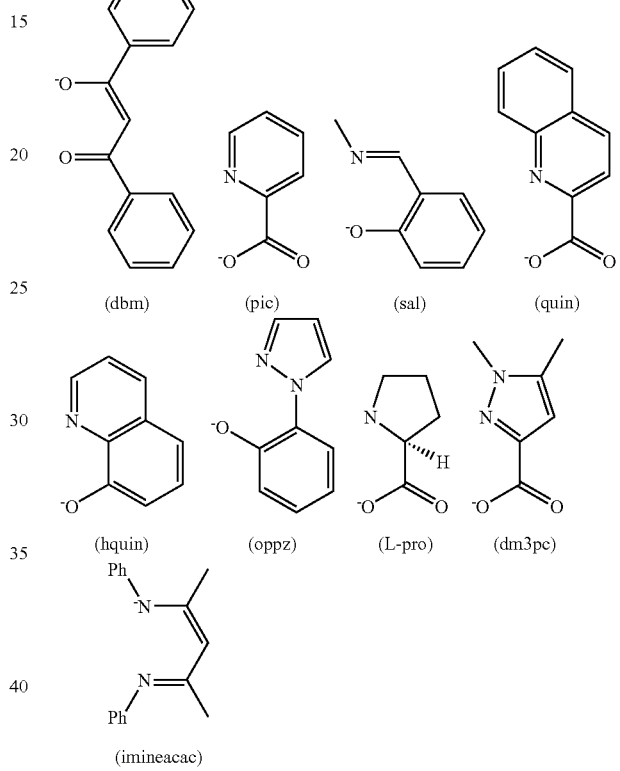

In the compound represented by formulas 2 or 3, A may be either —C($R_4$)— or —N—; $R_1$, $R_2$, and $R_4$ may all be H; $R_3$ may be H, or an electron donating group such as a methyl group, a methoxy group, an isopropyl group, a phenyloxy group, a benzyloxy group, a dimethylamino group, a diphenylamino group, a pyrrolidine group, or a phenyl group; B may be either —C($R_7$)— or —N—; $R_5$, $R_6$, and $R_7$ may each independently be H, or an electron withdrawing group such as F, a cyano group, a nitro group, a substituted benzene with F or a trifluoro methyl group, or a trifluoro methyl group; and X may be a material such as acetylacetonate (acac), hexafluoroacetylacetonate (hfacac), picolinate (pic), salicylanilide (sal), quinoline carboxylate (quin), 8-hydroxyquinolinate (hquin), L-proline (L-pro), 1,5-dimethyl-3-pyrazolecarboxylate (dm3pc), imineacetylacetonate (imineacac), dibenzoylmethane (dbm), tetrametyl heptandionate (tmd), 1-(2-hydoxyphenyl) pyrazolate (oppz), or phenylpyrazole (ppz).

In formulas 1-3, when A is either —C($R_4$)— or —N— and all of $R_1$, $R_2$, and $R_4$ are H, $R_3$ may be H, or an electron donating group such as a methyl group, a methoxy group, an isopropyl group, a phenyloxy group, a benzyloxy group, dimethylamino group, a diphenylamino group, a pyrrolidine group, or a phenyl group; B may be either —C(R$_7$)— or —N—; and R$_5$, R$_6$, and R$_7$ may each be H, or an electron withdrawing group such as F, a cyano group, a nitro group, a substituted benzene with F or trifluoromethyl, or a trifluoromethyl group.

Examples for the synthesis of a first compound (19), a second compound (33), a third compound (136), a fourth compound (138), and a fifth compound (142) are described as examples. However, the present invention is not limited to these compounds. Tables 1 and 2 each show specific compounds represented by formulas 2 and 3.

The compounds represented by formulas 2 and 3 are blue phosphorescent emission compounds with excellent color purity and high emission efficiency.

TABLE 1

| Compound No. | A | B | R1 | R2 | R3 | R4 | R5 | R6 | R7 | X |
|---|---|---|---|---|---|---|---|---|---|---|
| 1 | C | C | H | H | H | H | F | H | H | acac |
| 2 | C | C | H | H | H | H | F | F | H | acac |
| 3 | C | C | H | H | H | H | F | F | CN | acac |
| 4 | C | C | H | H | Methyl | H | F | H | H | acac |
| 5 | C | C | H | H | Methyl | H | F | F | H | acac |
| 6 | C | C | H | H | Methyl | H | F | F | CN | acac |
| 7 | C | C | H | H | Dimethylamin | H | F | H | H | acac |
| 8 | C | C | H | H | Dimethylamin | H | F | F | H | acac |
| 9 | C | C | H | H | Pyrrolidine | H | F | H | H | acac |
| 10 | C | C | H | H | Pyrrolidine | H | F | F | H | acac |
| 11 | C | C | H | H | Phenyl | H | F | H | H | acac |
| 12 | C | C | H | H | Phenyl | H | F | F | H | acac |
| 13 | C | C | H | H | CH3O | H | F | H | H | acac |
| 14 | C | C | H | H | CH3O | H | F | F | H | acac |
| 15 | C | C | H | H | H | H | F | H | H | pic |
| 16 | C | C | H | H | H | H | F | F | H | pic |
| 17 | C | C | H | H | H | H | F | F | CN | pic |
| 18 | C | C | H | H | Methyl | H | F | H | H | pic |
| 19 | C | C | H | H | Methyl | H | F | F | H | pic |
| 20 | C | C | H | H | Methyl | H | F | F | CN | pic |
| 21 | C | C | H | H | Dimethylamin | H | F | H | H | pic |
| 22 | C | C | H | H | Dimethylamin | H | F | F | H | pic |
| 23 | C | C | H | H | Pyrrolidine | H | F | H | H | pic |
| 24 | C | C | H | H | Pyrrolidine | H | F | F | H | Pic |
| 25 | C | C | H | H | Phenyl | H | F | H | H | Pic |
| 26 | C | C | H | H | Phenyl | H | F | F | H | Pic |
| 27 | C | C | H | H | CH3O | H | F | H | H | Pic |
| 28 | C | C | H | H | CH3O | H | F | F | H | Pic |
| 29 | C | C | H | H | H | H | F | H | H | dm3p |
| 30 | C | C | H | H | H | H | F | F | H | dm3p |
| 31 | C | C | H | H | H | H | F | F | CN | dm3p |
| 32 | C | C | H | H | Methyl | H | F | H | H | dm3p |
| 33 | C | C | H | H | Methyl | H | F | F | H | dm3p |
| 34 | C | C | H | H | Methyl | H | F | F | CN | dm3p |
| 35 | C | C | H | H | Dimethylamino | H | F | H | H | dm3p |
| 36 | C | C | H | H | Dimethylamino | H | F | F | H | dm3p |
| 37 | C | C | H | H | Pyrrolidine | H | F | H | H | dm3p |
| 38 | C | C | H | H | Pyrrolidine | H | F | F | H | dm3p |
| 39 | C | C | H | H | Phenyl | H | F | H | H | dm3p |
| 40 | C | C | H | H | Phenyl | H | F | F | H | dm3p |
| 41 | C | C | H | H | CH3O | H | F | H | H | dm3p |
| 42 | C | C | H | H | CH3O | H | F | F | H | dm2p |
| 43 | C | C | H | H | H | H | F | H | H | ppz |
| 44 | C | C | H | H | H | H | F | F | H | ppz |
| 45 | C | C | H | H | H | H | F | F | CN | ppz |
| 46 | C | C | H | H | Methyl | H | F | H | H | ppz |
| 47 | C | C | H | H | Methyl | H | F | F | H | ppz |
| 48 | C | C | H | H | Methyl | H | F | F | CN | ppz |
| 49 | C | C | H | H | Dimethylamino | H | F | H | H | ppz |
| 50 | C | C | H | H | Dimethylamino | H | F | F | H | ppz |
| 51 | C | C | H | H | Pyrrolidine | H | F | H | H | ppz |
| 52 | C | C | H | H | Pyrrolidine | H | F | F | H | ppz |
| 53 | C | C | H | H | Phenyl | H | F | H | H | ppz |
| 54 | C | C | H | H | Phenyl | H | F | F | H | ppz |
| 55 | C | C | H | H | CH3O | H | F | H | H | ppz |
| 56 | C | C | H | H | CH3O | H | F | F | H | ppz |

TABLE 1-continued

| Compound No. | A | B | R1 | R2 | R3 | R4 | R5 | R6 | X |
|---|---|---|---|---|---|---|---|---|---|
| 57 | C | N | H | H | H | H | F | H | acac |
| 58 | C | N | H | H | H | H | H | F | acac |
| 59 | C | N | H | H | H | H | F | F | acac |
| 60 | C | N | H | H | Methyl | H | F | H | acac |
| 61 | C | N | H | H | Methyl | H | H | F | acac |
| 62 | C | N | H | H | Methyl | H | F | F | acac |
| 63 | C | N | H | H | Dimethylamino | H | F | H | acac |
| 64 | C | N | H | H | Dimethylamino | H | F | F | acac |
| 65 | C | N | H | H | Pyrrolidine | H | F | H | acac |
| 66 | C | N | H | H | Pyrrolidine | H | F | F | acac |
| 67 | C | N | H | H | Phenyl | H | F | H | acac |
| 68 | C | N | H | H | Phenyl | H | F | F | acac |
| 69 | C | N | H | H | CH3O | H | F | H | acac |
| 70 | C | N | H | H | CH3O | H | F | F | acac |
| 71 | C | N | H | H | H | H | F | H | pic |
| 72 | C | N | H | H | H | H | F | F | pic |
| 73 | C | N | H | H | H | H | F | H | pic |
| 74 | C | N | H | H | Methyl | H | F | F | pic |
| 75 | C | N | H | H | Methyl | H | F | H | pic |
| 76 | C | N | H | H | Methyl | H | F | F | pic |
| 77 | C | N | H | H | Dimethylamino | H | F | H | pic |
| 78 | C | N | H | H | Dimethylamino | H | F | F | pic |
| 79 | C | N | H | H | Pyrrolidine | H | F | H | pic |
| 80 | C | N | H | H | Pyrrolidine | H | F | F | pic |
| 81 | C | N | H | H | Phenyl | H | F | H | pic |
| 82 | C | N | H | H | Phenyl | H | F | F | pic |
| 83 | C | N | H | H | CH3O | H | F | H | pic |
| 84 | C | N | H | H | CH3O | H | F | F | pic |
| 85 | C | N | H | H | H | H | F | H | dm3pc |
| 86 | C | N | H | H | H | H | H | F | dm3pc |
| 87 | C | N | H | H | H | H | F | F | dm3pc |
| 88 | C | N | H | H | Methyl | H | F | H | dm3pc |
| 89 | C | N | H | H | Methyl | H | H | F | dm3pc |
| 90 | C | N | H | H | Methyl | H | F | F | dm3pc |
| 91 | C | N | H | H | Dimethylamino | H | F | H | dm3pc |
| 92 | C | N | H | H | Dimethylamino | H | F | F | dm3pc |
| 93 | C | N | H | H | Pyrrolidine | H | F | H | dm3pc |
| 94 | C | N | H | H | Pyrrolidine | H | F | F | dm3pc |
| 95 | C | N | H | H | Phenyl | H | F | H | dm3pc |
| 96 | C | N | H | H | Phenyl | H | F | F | dm3pc |
| 97 | C | N | H | H | CH3O | H | F | H | dm3pc |
| 98 | C | N | H | H | CH3O | H | F | F | dm2pc |
| 99 | C | N | H | H | H | H | F | H | ppz |
| 100 | C | N | H | H | H | H | F | F | ppz |
| 101 | C | N | H | H | H | H | F | H | ppz |
| 102 | C | N | H | H | Methyl | H | F | F | ppz |
| 103 | C | N | H | H | Methyl | H | F | H | ppz |
| 104 | C | N | H | H | Methyl | H | F | F | ppz |
| 105 | C | N | H | H | Dimethylamino | H | F | H | ppz |
| 106 | C | N | H | H | Dimethylamino | H | F | F | ppz |
| 107 | C | N | H | H | Pyrrolidine | H | F | H | ppz |
| 108 | C | N | H | H | Pyrrolidine | H | F | F | ppz |
| 109 | C | N | H | H | Phenyl | H | F | H | ppz |
| 110 | C | N | H | H | Phenyl | H | F | F | ppz |
| 111 | C | N | H | H | CH3O | H | F | H | ppz |
| 112 | C | N | H | H | CH3O | H | F | F | ppz |

| Compound No. | A | B | R1 | R2 | R3 | R5 | R6 | R7 | X |
|---|---|---|---|---|---|---|---|---|---|
| 113 | N | C | H | H | H | F | H | H | acac |
| 114 | N | C | H | H | H | F | F | H | acac |
| 115 | N | C | H | H | H | F | F | CN | acac |
| 116 | N | C | H | H | H | F | H | H | pic |
| 117 | N | C | H | H | H | F | F | H | pic |
| 118 | N | C | H | H | H | F | F | CN | pic |
| 119 | N | C | H | H | H | F | H | H | dm3pc |
| 120 | N | C | H | H | H | F | F | H | dm3pc |
| 121 | N | C | H | H | H | F | F | CN | dm3pc |
| 122 | N | C | H | H | H | F | H | H | ppz |
| 123 | N | C | H | H | H | F | F | H | ppz |
| 124 | N | C | H | H | H | F | F | CN | ppz |

TABLE 1-continued

| Compound No. | A | B | R1 | R2 | R3 | R4 | R5 | R6 | X |
|---|---|---|---|---|---|---|---|---|---|
| 125 | C | N | H | H | H | H | H | H | pic |
| 126 | C | N | H | H | H | H | F | H | pic |
| 127 | C | N | H | H | H | H | H | F | pic |
| 128 | C | N | H | H | H | H | F | F | pic |
| 129 | C | N | H | H | H | H | F | CN | pic |
| 130 | C | N | H | H | H | H | H | H | ppz |
| 131 | C | N | H | H | H | H | F | H | ppz |
| 132 | C | N | H | H | H | H | H | F | ppz |
| 133 | C | N | H | H | H | H | F | F | ppz |
| 134 | C | N | H | H | H | H | F | CN | ppz |

TABLE 2

| Compound No. | A | B | R1 | R2 | R3 | R4 | R5 | R6 | R7 |
|---|---|---|---|---|---|---|---|---|---|
| 135 | C | C | H | H | H | H | F | H | H |
| 136 | C | C | H | H | H | H | F | F | H |
| 137 | C | C | H | H | H | H | F | F | CN |
| 138 | C | C | H | H | Methyl | H | F | H | H |
| 139 | C | C | H | H | Methyl | H | H | F | H |
| 140 | C | C | H | H | Methyl | H | F | F | CN |
| 141 | C | C | H | H | Dimethylamin | H | F | H | H |
| 142 | C | C | H | H | Dimethylamin | H | F | F | H |
| 143 | C | C | H | H | Pyrrolidine | H | F | H | H |
| 144 | C | C | H | H | Pyrrolidine | H | F | F | H |
| 145 | C | C | H | H | Phenyl | H | F | H | H |
| 146 | C | C | H | H | Phenyl | H | F | F | H |
| 147 | C | C | H | H | CH3O | H | F | H | H |
| 148 | C | C | H | H | CH3O | H | F | F | H |
| 149 | C | C | H | H | H | H | F | H | H |
| 150 | C | C | H | H | H | H | F | F | H |
| 151 | C | C | H | H | H | H | F | F | CN |
| 152 | C | C | H | H | Methyl | H | F | H | H |
| 153 | C | C | H | H | Methyl | H | F | F | H |
| 154 | C | C | H | H | Methyl | H | F | F | CN |
| 155 | C | C | H | H | Dimethylamin | H | F | H | H |
| 156 | C | C | H | H | Dimethylamin | H | F | F | H |
| 157 | C | C | H | H | Pyrrolidine | H | F | H | H |
| 158 | C | C | H | H | Pyrrolidine | H | F | F | H |
| 159 | C | C | H | H | Phenyl | H | F | H | H |
| 160 | C | C | H | H | Phenyl | H | F | F | H |
| 161 | C | C | H | H | CH3O | H | F | H | H |
| 162 | C | C | H | H | CH3O | H | F | F | H |

| Compound No. | A | B | R1 | R2 | R3 | R4 | R5 | R6 |
|---|---|---|---|---|---|---|---|---|
| 163 | C | N | H | H | H | H | F | H |
| 164 | C | N | H | H | H | H | H | F |
| 165 | C | N | H | H | H | H | F | F |
| 166 | C | N | H | H | Methyl | H | F | H |
| 167 | C | N | H | H | Methyl | H | H | F |
| 168 | C | N | H | H | Methyl | H | F | F |
| 169 | C | N | H | H | Dimethylamino | H | F | H |
| 170 | C | N | H | H | Dimethylamino | H | F | F |
| 171 | C | N | H | H | Pyrrolidine | H | F | H |
| 172 | C | N | H | H | Pyrrolidine | H | F | F |
| 173 | C | N | H | H | Phenyl | H | F | H |
| 174 | C | N | H | H | Phenyl | H | F | F |
| 175 | C | N | H | H | CH3O | H | F | H |
| 176 | C | N | H | H | CH3O | H | F | F |
| 177 | C | N | H | H | H | H | F | H |
| 178 | C | N | H | H | H | H | F | F |
| 179 | C | N | H | H | H | H | F | H |
| 180 | C | N | H | H | Methyl | H | F | F |
| 181 | C | N | H | H | Methyl | H | F | H |
| 182 | C | N | H | H | Methyl | H | F | F |
| 183 | C | N | H | H | Dimethylamino | H | F | H |
| 184 | C | N | H | H | Dimethylamino | H | F | F |
| 185 | C | N | H | H | Pyrrolidine | H | F | H |
| 186 | C | N | H | H | Pyrrolidine | H | F | F |
| 187 | C | N | H | H | Phenyl | H | F | H |
| 188 | C | N | H | H | Phenyl | H | F | F |
| 189 | C | N | H | H | CH3O | H | F | H |
| 190 | C | N | H | H | CH3O | H | F | F |

| Compound No. | A | B | R1 | R2 | R3 | R5 | R6 | R7 |
|---|---|---|---|---|---|---|---|---|
| 191 | N | C | H | H | H | F | H | H |
| 192 | N | C | H | H | H | F | F | H |
| 193 | N | C | H | H | H | F | F | CN |

| Compound No. | A | B | R1 | R2 | R3 | R4 | R5 | R6 |
|---|---|---|---|---|---|---|---|---|
| 194 | C | N | H | H | H | H | H | H |
| 195 | C | N | H | H | H | H | F | H |
| 196 | C | N | H | H | H | H | H | F |
| 197 | C | N | H | H | H | H | F | F |
| 198 | C | N | H | H | H | H | F | CN |

| Compound No. | A | B | R1 | R2 | R3 | R5 | R6 |
|---|---|---|---|---|---|---|---|
| 199 | N | N | H | H | H | H | H |
| 200 | N | N | H | H | H | F | H |
| 201 | N | N | H | H | H | H | F |
| 202 | N | N | H | H | H | F | F |
| 203 | N | N | H | H | H | F | CN |

Reaction Scheme 1 can aid in understanding a method of manufacturing the Ir represented by formula 1.

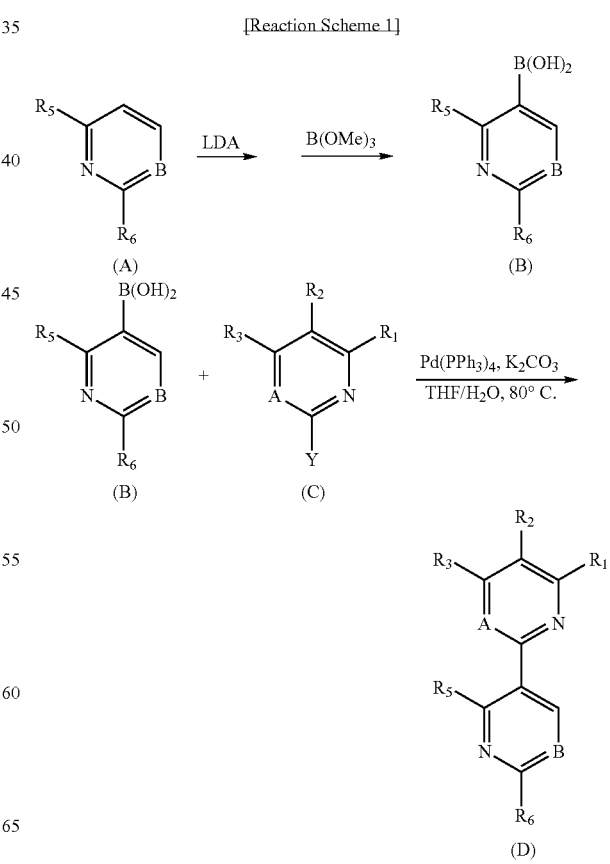

[Reaction Scheme 1]

-continued

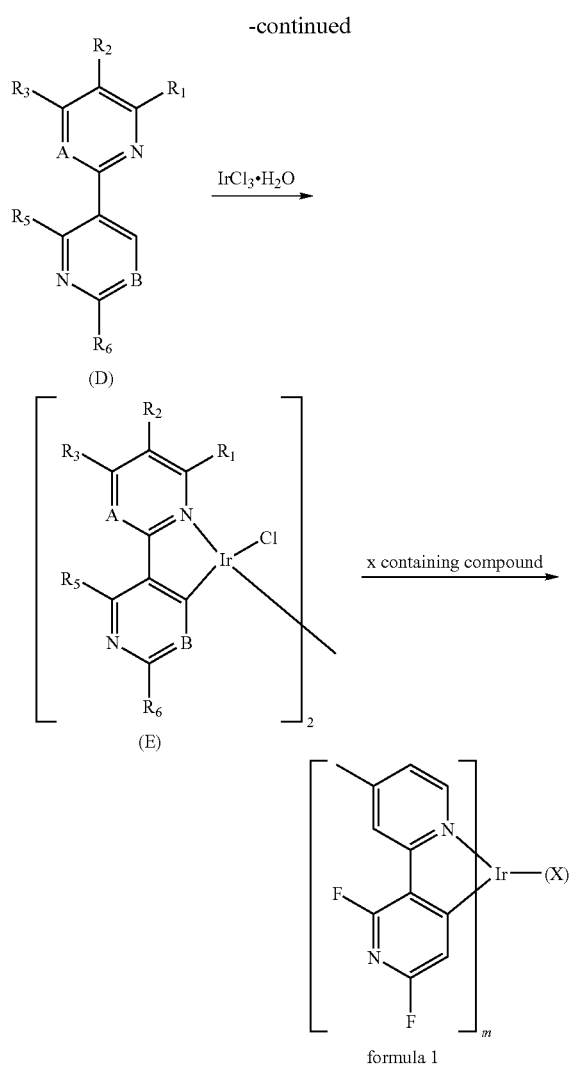

formula 1 in which Y may be a halogen atom such as Br and Cl.

First, a pyridine compound (A) may be made to react with an organic lithium compound such as lithium diisopropylamide or a borone compound such as a trimethylborate to produce a compound (B).

The compound (B) may be made to react with a compound (C) in the presence of tetrakistriphenylphosphinepalladium and a base to produce a compound (D). The compound (D) may be made to react with Ir chloride to produce a dimer (E).

The dimer (E) may be made to react with an X-containing compound to produce an Ir compound presented by formula 1.

As shown in FIG. 1, an organic electroluminescent device can be manufactured. First, an anode forming material may be coated on a substrate to form an anode. Any substrate that is commonly used in a conventional organic EL device can be used. The substrate may be a glass substrate or a transparent plastic substrate. Glass substrates or transparent plastic substrates have excellent transparent characteristics, surface smoothness, and waterproof characteristics. The anode forming material may be indium tin oxide (ITO), indium zinc oxide (IZO), $SnO_2$, or ZnO.

A hole injection layer forming material may be applied to an upper surface of the anode by a technique such as vacuum thermal deposition or spin coating to form a hole injection layer(HIL). The (HIL) may be composed of CuPc represented by, for example, the following formula or a starburst type amine. The starburst type amine may be TCTA, m-MTDATA, IDE406 (obtained from IDEMITSU CO.), or the like. In this case, TCTA and m-MTDATA are represented by the following formulas:

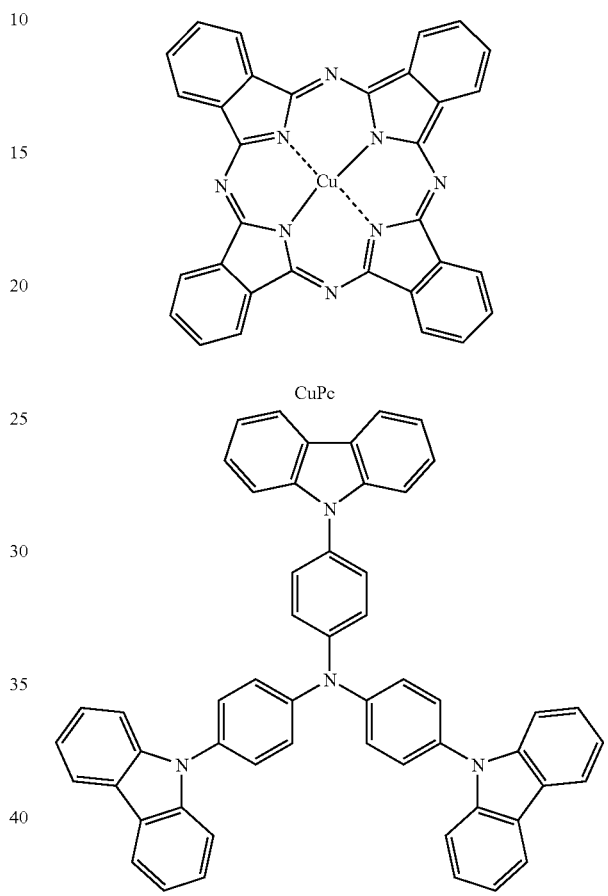

CuPc

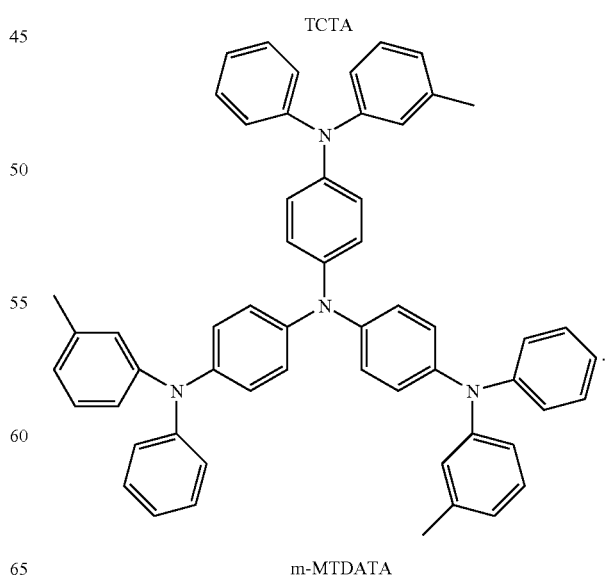

TCTA m-MTDATA

A hole transporting layer forming material may be, for example, vacuum hot deposited or spin coated on the HIL to form a hole transporting layer (HTL). The HTL may be composed of N,N'-bis(3-methylphenyl)-N,N'-diphenyl-[1,1-biphenyl]-4,4'-diamine (TPD), N,N'-di(naphtalene-1-yl)-N,N'-diphenyl benzidine, N,N'-di(naphtalene-1-yl)-N,N'-diphenyl-benxidine (α-NPD), IDE320 (obtained from IDEMITSU CO.), or the like. In this example, TPD and α-NPD are represented by the following formula. However, the HTL can be composed of other materials.

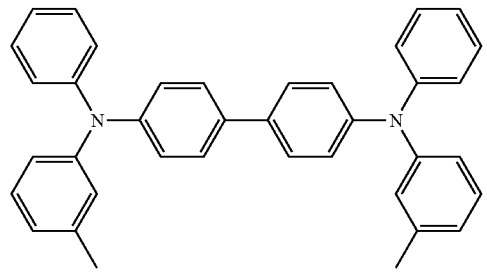

TPD

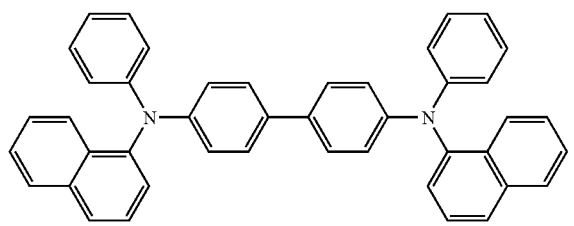

α-NPD

A light emitting layer (EML) may be formed on the HTL. The compound represented formula 1 can be used (alone, or as a dopant) to form the EML. However, the EML can be composed of other materials. When the compound represented formula 1 is used as a dopant, a host includes CBP, TCB, TCTA, SDI-BH-18, SDI-BH-19, SDI-BH-22, SDI-BH-23, dmCBP, Liq, TPBI, Balq, BCP, or the mixture thereof. The dopant and the host may be applied to an upper surface of the hole transport layer by vacuum thermal co-deposition to form an EML. In this case, CBP, TCB, TCTA, SDI-BH-18, SDI-BH-19, SDI-BH-22, SDI-BH-23, dmCBP, Liq, TPBI, Balq, and BCP are represented by the following formulas.

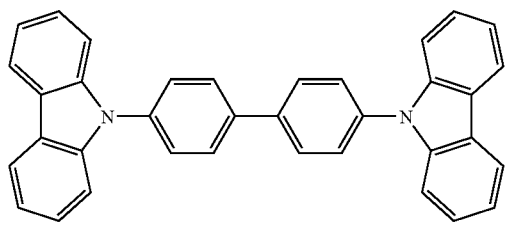

CBP

-continued

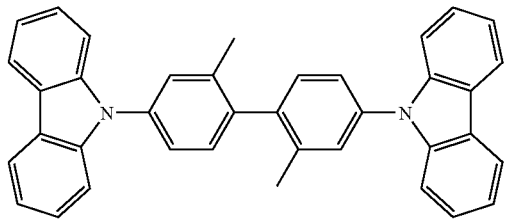

dmCBP

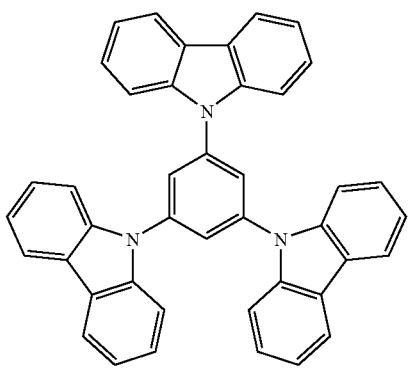

TCB

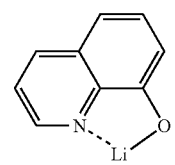

Liq

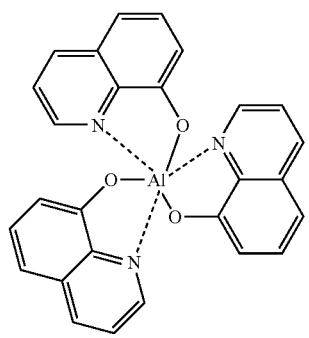

Alq3

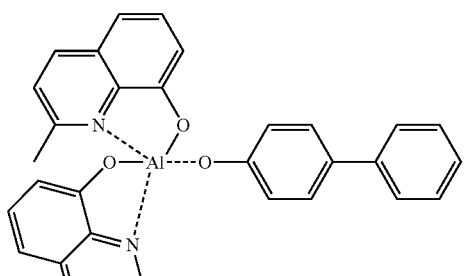

Balq

-continued

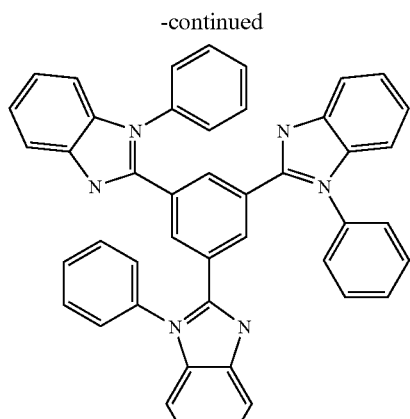
TPBI

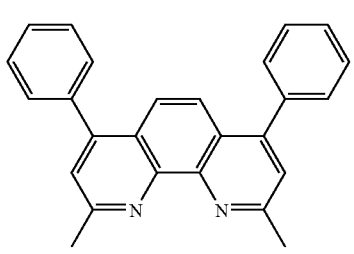
BCP

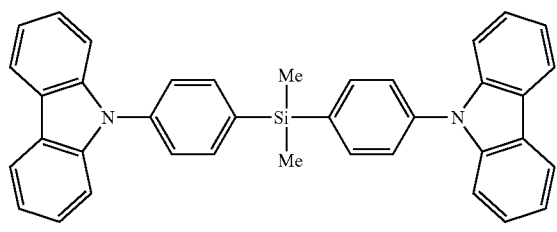
SDI-BH-18

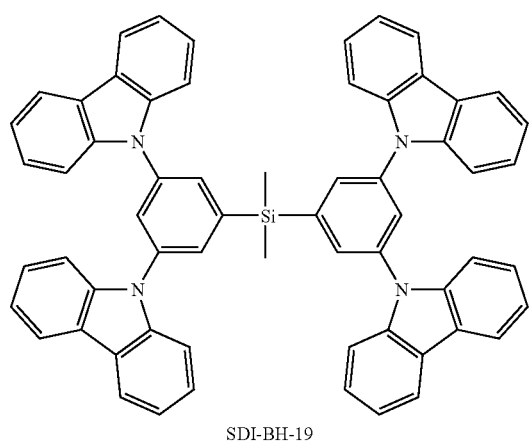
SDI-BH-19

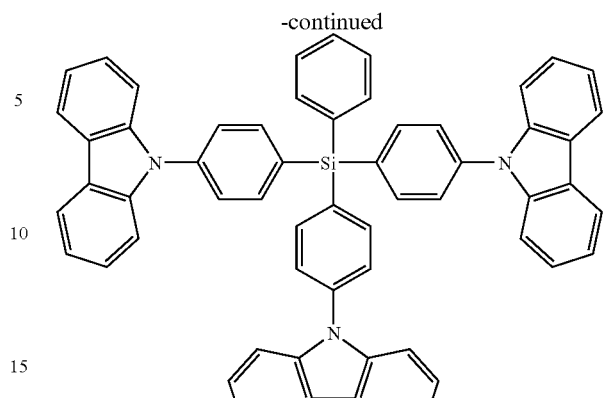
SDI-BH-22

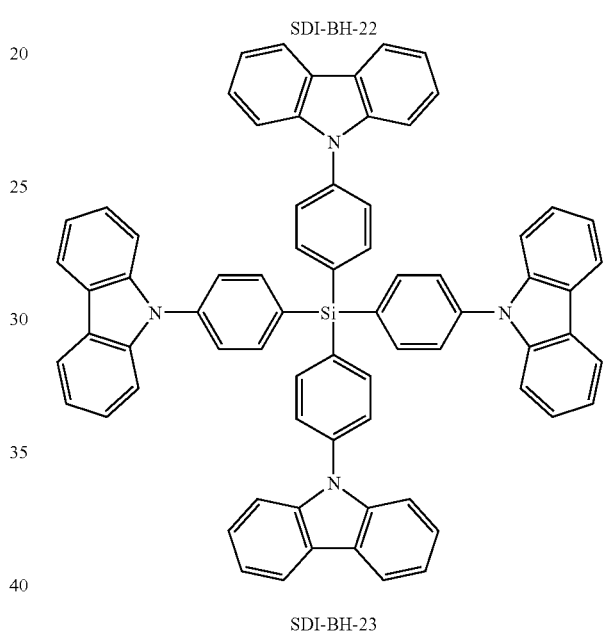
SDI-BH-23

When the compound represented by formula 1 is used as a dopant, the amount of dopant may be in the range of 1-20 parts by weight based on 100 parts by weight of the host and the dopant. However, the amount of dopant may not be limited thereto. A hole blocking layer (HBL) may be formed on the EML by vacuum deposition or spin coating. The HBL forming material should have electron transporting capacity, and a higher ionization potentional than the light emitting compound. The HBL may, for example, be composed of Balq, BCP, TPBI, or the like.

An electron transporting layer (ETL) may be formed on the HBL by vacuum deposition or spin coating. The ETL may be composed of, for example, Alq3. An (EIL) may be formed on the ETL. The EIL may be composed of LiF, NaCl, CsF, $Li_2O$, BaO, Liq, or the like.

A cathode forming metal may be vacuum hot deposited on the EIL to form a cathode. Therefore, an organic EL device may be completed. The cathode forming metal may be Li, Mg, Al, Al—Li, Ca, Mg—In, Mg—Ag, or the like. In addition, to obtain a front emission device, a cathode can be composed of ITO or IZO. Such a cathode may be transparent. The organic EL device may include one or more intermediate layers between the anode, the HIL, the HTL, the EML, the HBL, the ETL, the EIL, and the cathode, when needed. In addition, an electron blocking layer (EBL) can be further formed.

The present invention will be described in further detail with reference to the following examples. The following examples are for illustrative purposes, and are not intended to limit the scope of the present invention.

SYNTHESIS EXAMPLE 1

Synthesis of Intermediates of (B-1) and (E-1)

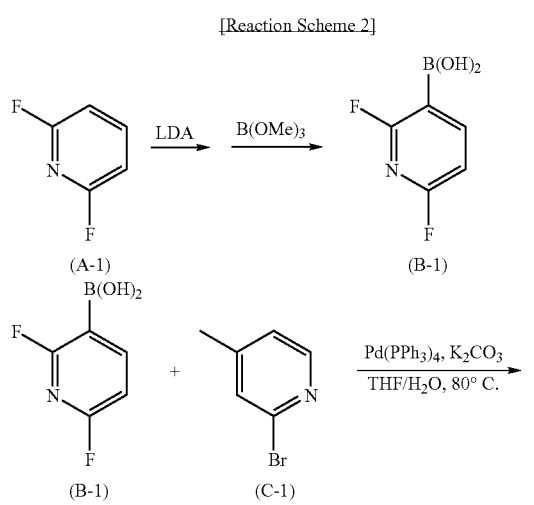

1) Synthesis of Intermediate (D-1)

Lithium diisopropylamide (LDA), in an amount of 6.0 ml (12.0 mmol), was added to 50 ml of diethylether. Difluoropyridine, in an amount of 0.91 ml (10.0 mmol), was added dropwise at −78° C., and stirred for one hour. Trimethylborate, in an amount of 1.4 ml (12.5 mmol), was added to the resultant mixture, and stirred at room temperature for one hour.

After the reaction was completed, 20 ml of 5% NaOH aqueous solution were added to the reaction mixture. The reaction mixture was separated into an organic layer and an aqueous solution layer. The aqueous solution layer was neutralized using a 3N HCl aqueous solution. The neutralized aqueous solution layer was extracted using 20 ml of ethylacetate. This extracting process was repeated thrice to obtain an organic layer. The organic layer was dried over MgSO₄. The resultant remains were dried again in a vacuum state to attain white solid of an intermediate (B-1). The amount of B-1 was 1.03 g (yield: 65%).

In 18 ml of THF, 570 mg (3.587 mmol) of B-1 and 0.4 ml (3.0 mmol) of 2-bromo-4-methylpyridine (C-1) were dissolved. Then, 200 mg (0.18 mmol) of tetrakistriphenylphosphinepalladium, 2.48 g (17.9 mmol) of K₂CO₃ dissolved in 10 ml of distilled water were added to the mixture, and stirred at 75° C. for 12 hours. The resultant mixture was extracted using 10 ml of ethylacetate. This extracting process was repeated thrice to obtain an organic layer. The organic layer was dried over MgSO₄ and a solvent was removed to obtain a crude product. The resultant crude product was purified using silicagel column chromatography to attain a compound (D-1). The amount of D-1 was 544 mg (yield: 88%). D-1 was identified using ¹H NMR.

¹H NMR (CDCl₃, 400 MHz) δ(ppm) 8.68-8.62 (m, 1H), 8.57 (d, J=5.12 Hz, 1H) 7.67 (s, 1H), 7.13 (d, J=4.96 Hz, 1H), 6.98-6.95 (m, 1H), 2.44 (s, 3H)

Synthesis of Intermediate (E-1)

In 45 ml of 2-ethoxyethanol, 2.0 g (9.70 mmol) of the intermediate (D-1) were dissolved. Then, 1.45 g of Irchloridehydrate and 15 ml of distilled water were added to the mixture, and stirred at 120° C. for 24 hours. After the reaction was completed, the reaction mixture was cooled to room temperature to produce a precipitate. The precipitate was washed with methanol, and then dried in a vacuum state to attain 1.30 g of an intermediate (E-1).

SYNTHESIS EXAMPLE 2

Synthesis of First Compound (19)

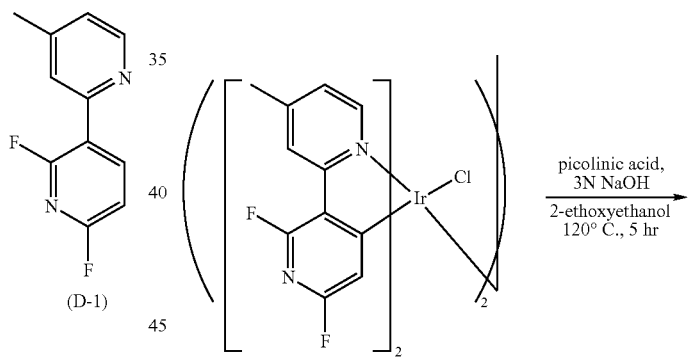

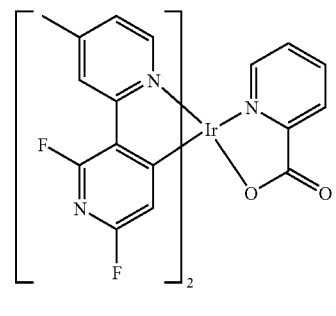

In 2-ethoxyethanol, 300 mg (0.47 mmol) of the intermediate (E-1), 174 mg (1.41 mmol) of picolinic acid, 0.24 ml (0.71 mmol) of a 3N NaOH aqueous solution were dissolved, and then stirred at 120° C. for 5 hours. After the reaction was completed, the 2-ethoxyethanol was removed from the reaction mixture. The result was diluted using dichloro methane, and then washed with distilled water. The result was separated into an organic layer and an aqueous solution layer. The organic layer was dried over MgSO$_4$ and the solvent was removed. The resultant was purified using recrystallization to attain a first compound (19). The amount of the first compound (19) was 230 mg (yield: 68%). The first compound (19) was identified using $^1$H-NMR.

$^1$H NMR (CDCl$_3$, 400 MHz) δ(ppm) 8.58 (d, J=6.04 Hz, 1H), 8.36 (d, J=7.72 Hz, 1H), 8.14 (s, 1H), 8.08 (s, 1H), 8.01 (dd, J=7.68, 7.72 Hz, 1H), 7.77 (d, J=5.52 Hz, 1H), 7.49 (dd, J=6.80, 6.20 Hz, 1H), 7.25 (s, 1H), 7.129 (d, J=5.84 Hz, 1H), 6.91 (d, J=5.32 Hz, 1H), 5.84 (s, 1H), 5.57 (s, 1H), 2.61 (s, 3H), 2.60 (s, 3H)

SYNTHESIS EXAMPLE 3

Synthesis of Second Compound (33)

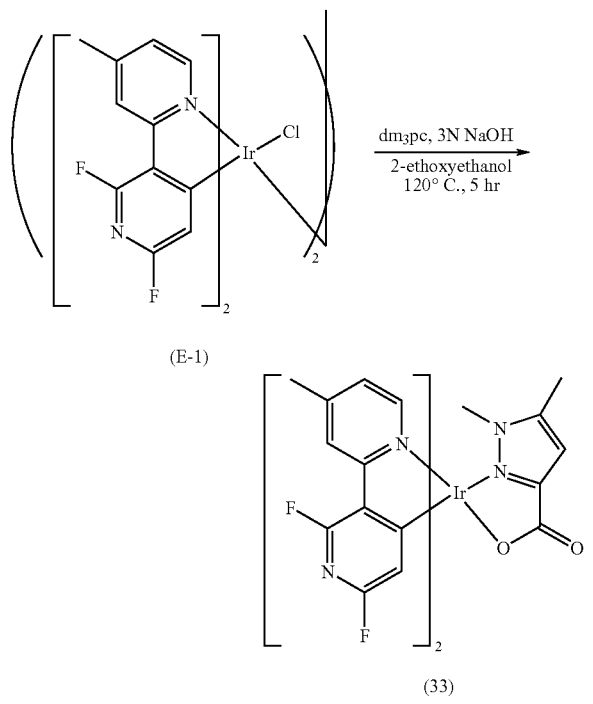

In 2-ethoxyethanol, 700 mg (0.911 mmol) of the intermediate (E-1), 383 mg (2.73 mmol) of 1,5-dimethyl-1H-pyrazole-3-carboxylic acid (dm3pc), 0.46 ml (1.37 mmol) of a 3N NaOH aqueous solution were dissolved, and then stirred at 120° C. for 5 hours. After the reaction was completed, the 2-ethoxyethanol was removed from the reaction mixture. The result was diluted using dichloro methane, and then washed with distilled water. The result was separated into an organic layer and an aqueous solution layer. The organic layer was dried using MgSO$_4$ to remove a solvent. The resultant remains were refined using recrystallization to attain a second compound (33). The amount of the second compound (33) was 620 mg (yield: 92%). The second compound (33) was identified using 1H-NMR.

$^1$H NMR (CDCl3, 400 MHz) δ (ppm) 8.63 (d, J=5.84 Hz, 1H), 8.11 (s, 2H), 7.41 (d, J=5.88 Hz, 1H), 7.17 (d, J=5.52 Hz, 1H), 6.98 (d, J=5.12 Hz, 1H), 6.60 (s, 1H), 5.86 (s, 1H), 5.45 (s, 1H), 3.14 (s, 3H), 2.65 (s, 3H), 2.61 (s, 3H), 2.32 (s, 3H)

SYNTHESIS EXAMPLE 4

Synthesis of Intermediate (D-2)

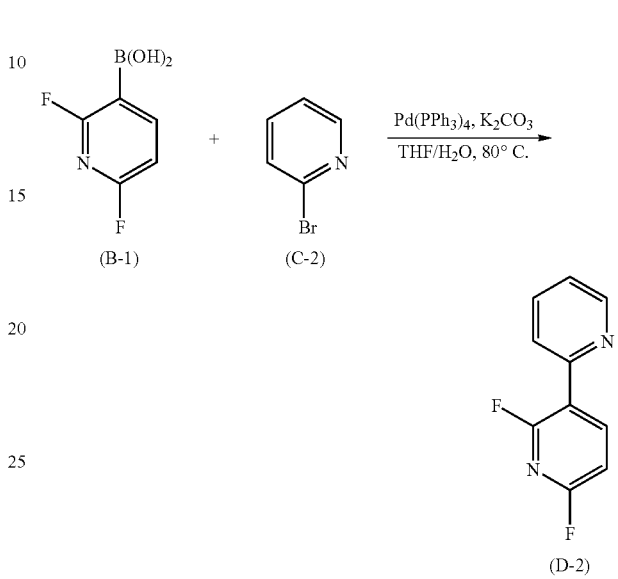

In 18 ml of THF, 570 mg (3.587 mmol) of the intermediate (B-1) and 0.4 ml (3.0 mmol) of 2-bromopyridine (C-2) were dissolved. Then, 200 mg (0.18 mmol) of tetrakistriphenylphosphinepalladium, 2.48 g (17.9 mmol) of K$_2$CO$_3$ dissolved in 10 ml of distilled water were added to the mixture, and stirred at 75° C. for 12 hours. The resultant mixture was extracted using 10 ml of ethylacetate. This extracting process was repeated thrice to obtain an organic layer. The organic layer was dried over MgSO$_4$ and the solvent was removed. The resultant was refined using silicagel column chromatography to attain a compound (D-2). The amount of D-2 was 520 mg (yield: 90%). D-2 was identified using $^1$H NMR.

$^1$H NMR (CDCl$_3$, 400 MHz) δ(ppm) 7.30-7.10(m, 2H), 7.86-7.85 (m, 1H), 7.82-7.80 (m, 1H), 7.35-7.26 (m, 1H), 7.00-6.97 (m, 1H)

SYNTHESIS EXAMPLE 5

Synthesis of Third Compound (136) with a Meridional Structure

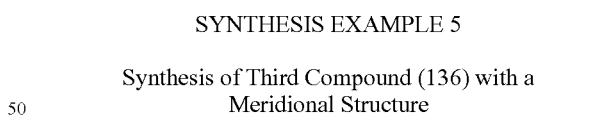
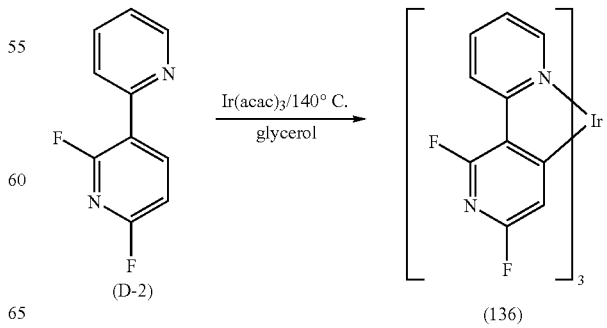

10 ml of glycerol was stirred at room temperature for 30 minutes, while N was injected thereto. Then, 100 mg (0.2 mmol) of Ir(acac)$_3$ and 940 mg (0.6 mmol) of D-2 were added thereto, and stirred at 140° C. for 24 hours while heating. After the reaction was completed, water was added to the reaction mixture, and the reaction product was filtered, and then washed with n-hexane. The result was dissolved in methylene chloride, and refined again using column chromatography. Then, the refined product was dried for 3 hours using a vacuum pump to attain a third compound (136) with a meridional structure. The yield of the compound with a meridional structure was 30%.

$^1$H NMR (CDCl$_3$, 400 MHz) δ (ppm) 8.0 (d, J=8.24 Hz, 1H), 8.31-8.27 (m, 2H), 7.97 (d, J=5.68 Hz, 1H), 7.92 (d, J=5.32 Hz, 1H), 7.87 (m, 1H), 7.80 -7.78 (m, 2H), 7.47 (d, J=5.16 Hz, 1H), 7.13 (m, 1H), 7.02 -6.97 (m, 2H), 6.33 (m, 1H), 5.92 (m, 1H, 5.70 (s, 1H)

SYNTHESIS 6

Synthesis of Third Compound (136) with a Facial Structure

At room temperature, 10 ml of glycerol was stirred for 30 minutes, while N was injected thereto. Then, 100 mg (0.2 mmol) of Ir(acac)$_3$ and 940 mg (0.6 mmol) of D-2 were added thereto, and stirred at 140° C. for 24 hours while heating. After the reaction was completed, water was added to the reaction mixture, and the reaction product was filtered and them washed with n-hexane. The result was dissolved in methylene chloride, and refined again using column chromatography. Then, the refined product was dried for 3 hours using a vacuum pump to attain a third compound (136) with a meridional structure. The yield of the compound with a meridional structure was 30%.

$^1$H NMR (CDCl$_3$, 400 MHz) δ (ppm) 8.37 (d, J=8.24 Hz, 1H), 7.86 (m, 1H), 7.46-7.45 (m, 1H), 7.13-7.09 (m, 1H), 6.21 (m, 1H)

SYNTHESIS 7

Synthesis of Fourth Compound (138) with a Meridional Structure

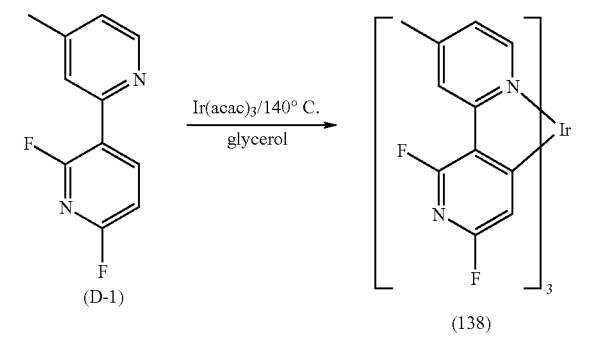

A fourth compound (138) with a meridional structure was prepared in the same manner of synthesizing the third compound (136) with a meridional structure. The yield of the fourth compound (138) with a meridional structure was 30%.

$^1$H NMR (CDCl$_3$, 400 MHz) δ (ppm) 8.17 (s, 1H),8.08 (s, 1H), 8.06 (s, 1H), 7.76 (d, J=5.88 Hz,1H), 7.72 (d, J=5.64 Hz, 1H), 7.30 (d, J=6.04, 1H), 6.91 (d, J=5.52 Hz, 1H), 6.79-6.76 (m, 2H), 6.31 (m, 1H), 5.93 (m, 1H), 5.73 (s, 1H), 2.51 (m, 9H)

SYNTHESIS 8

Synthesis of Fourth Compound (138) with a Facial Structure

A fourth compound (138) with a facial structure was prepared in the same manner of synthesizing the third compound (136) with a facial structure. The yield of the fourth compound (138) with a facial structure was 20%.

$^1$H NMR (CDCl$_3$, 400 MHz) δ (ppm) 8.14 (s, 1H), 7.30 (d, J=5.68 Hz, 1H), 690 (d, J=4.76 Hz, 1H), 2.50 (s, 3H)

SYNTHESIS EXAMPLE 9

Synthesis of Intermediate (D-3)

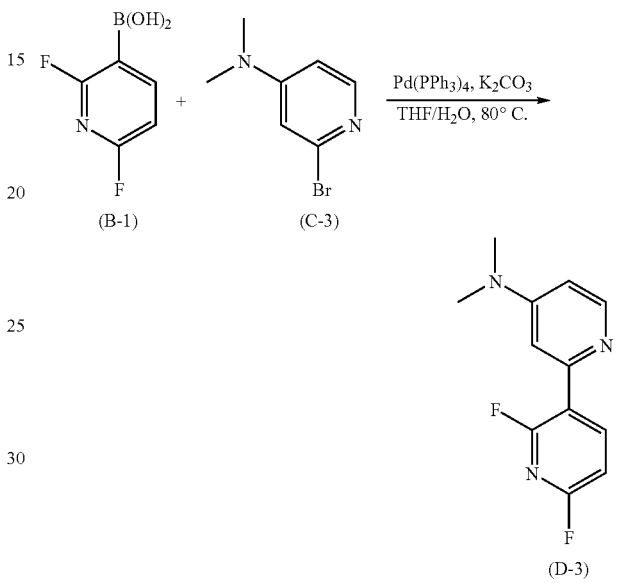

In 18 ml of THF, 570 mg (3.587 mmol) of the intermediate (B-1) and 0.4 ml (3.0 mmol) of 2-bromopyridine (C-3) were dissolved. Then, 200 mg (0.18 mmol) of tetrakistriphenylphosphinepalladium, 2.48 g (17.9 mmol) of K$_2$CO$_3$ dissolved in 10 ml of distilled water were added to the mixture, and stirred at 75° C. for 12 hours. The resultant mixture was extracted using 10 ml of ethylacetate. This extracting process was repeated thrice to obtain an organic layer. The organic layer was dried over MgSO$_4$. The resultant was refined using silicagel column chromatography to attain a compound (D-3). The amount of D-3 was 635 mg (yield: 90%). D-3 was identified using $^1$H NMR.

$^1$H NMR (CDCl$_3$, 400 MHz) δ (ppm) 8.64-8.58 (m, 1H), 8.31 (d, J=6.04 Hz, 1H), 7.04 (s, 1H), 6.94 (m, 1H), 6.50 (m, 1H), 3.06 (s, 6H)

SYNTHESIS 10

Synthesis of Fifth Compound (142) with a Meridional Structure

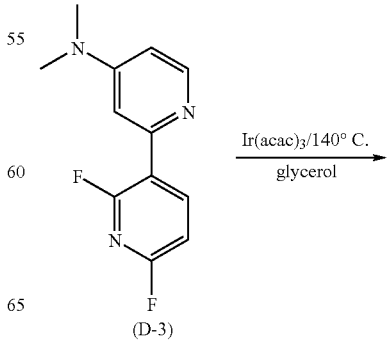

-continued

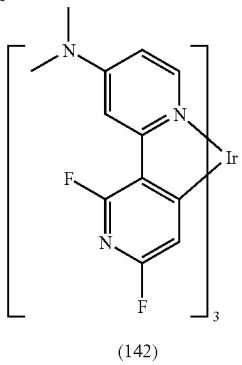

(142)

A fifth compound (142) with a meridional structure was prepared in the same manner of synthesizing the third compound (136) with a meridional structure. The yield of the fifth compound (142) with a meridional structure was 30%.

$^1$H NMR (CDCl$_3$, 400 MHz) δ(ppm) 7.50 (m, 1H), 7.44-7.41 (m, 4H), 7.11 (d, J=6.6 Hz, 1H), 6.33 (m, 1H), 6.22 (m, 1H), 6.17 (m, 1H), 6.13 (m, 1H), 6.06 (m, 1H), 5.89 (s, 1H), 3.10 (m, 18H)

EXAMPLE 1

Manufacture of Organic EL Device

A glass substrate of 15Ω/cm$^2$ (1200 Å) coming ITO was cut to a size of 50 mm×50 mm×0.7 mm, and was subjected to ultrasonic washing for 5 minutes in isopropyl alcohol and then for another 5 minutes in pure water. Then, the result was cleaned using UV ozone for 30 minutes. IDE406 (obtained from IDEMITSU CO.) was vacuum deposited on the ITO glass substrate to form a hole injection layer with a thickness of 600 Å. IDE320 (obtained from IDEMITSU CO.) was vacuum deposited on the hole injection layer to form a hole transporting layer with a thickness of 300 Å. 95 parts by weight of SDI-BH-23 as a light emitting layer host, and 5 parts by weight of a first compound (19) as a dopant were co-deposited in a vacuum state on the hole transporting layer to form a light emitting layer with a thickness of 300.

Balq was vacuum deposited on the light emitting layer to form a hole blocking layer with a thickness of 50 Å. Alq$_3$ was vacuum deposited on the hole blocking layer to form an electron transporting layer with a thickness of 200 Å. LiF was vacuum deposited on the electron transporting layer to form an electron injection layer with a thickness of 10 Å. Al was vacuum deposited on the electron injection layer to form a cathode with a thickness of 3000 Å. As a result, an organic EL device was completed.

Emission characteristics and color purity of the organic EL device were identified. The results are shown in FIGS. 2-5.

As shown in FIGS. 2-5, when the organic EL device was provided with a direct current of 7 V (the current density was 4.9 mA/cm$^2$), it exhibited an emission luminance of 101 cd/m$^2$, an emission efficiency of 2.0 cd/A, and a color coordinate of (0.171, 0.203). A blue emission with high color purity was attained.

In addition, 0.02 mM of the first compound (19) was prepared by diluting in CH$_2$Cl$_2$. A photoluminescence (PL) spectrum of the diluted solution was obtained by radiating 370nm UV. The results are shown in FIG. 6.

Figure 6:
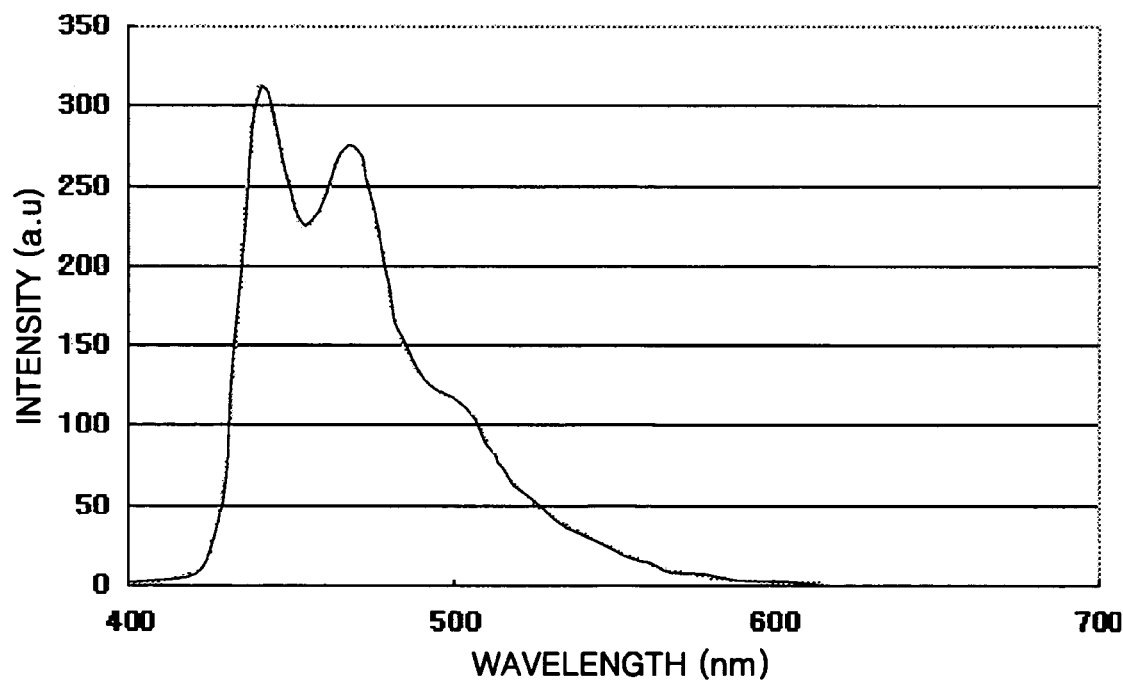
FIGS. 6, 11, 16, 21, 22, 23, and 24 illustrate photoluminescence (PL) spectra of a first compound (19), a second compound (33), a third compound (136) with a meridional structure, a third compound (136) with a facial structure, a fourth compound (138) with a meridional structure, a fourth compound (138) with a facial structure, and a fifth compound (142), respectively, all of the forgoing compounds being prepared according to the present invention.
Figure 7:
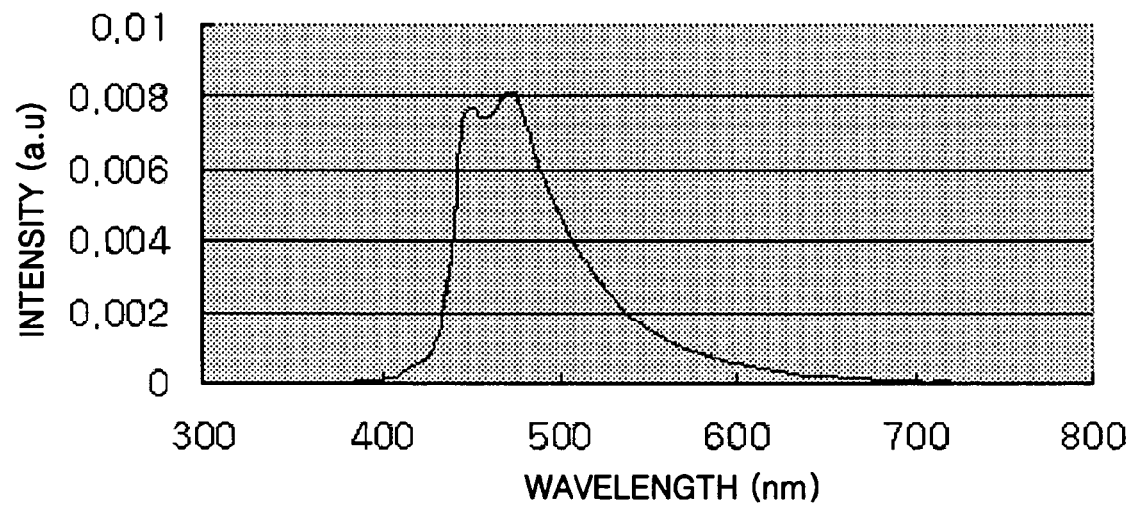
Figure 8:
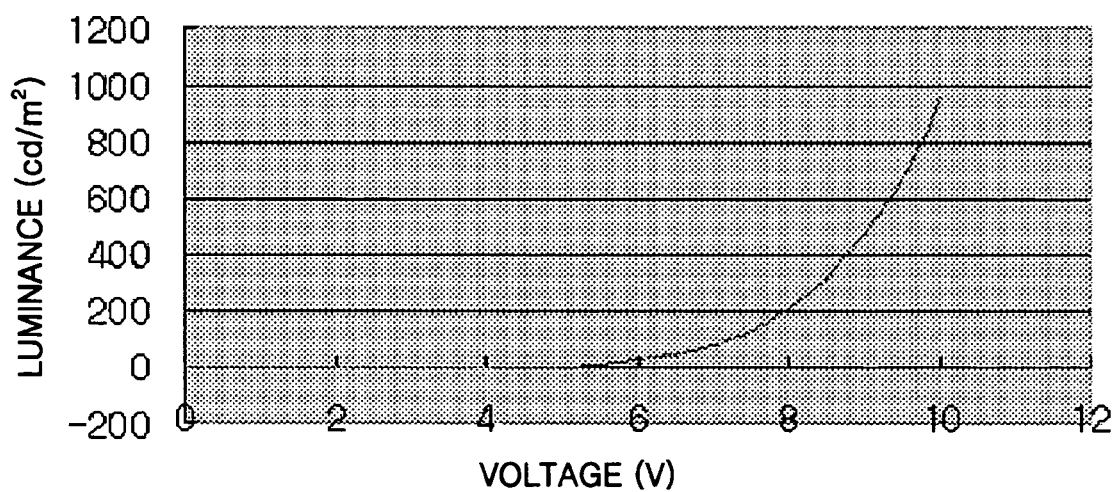
Figure 9:
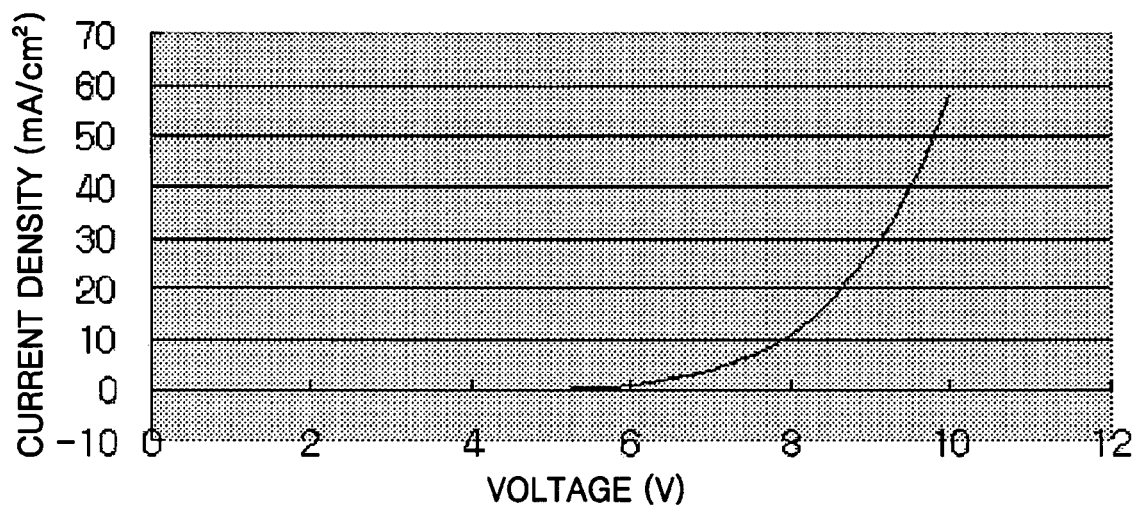
Figure 10:
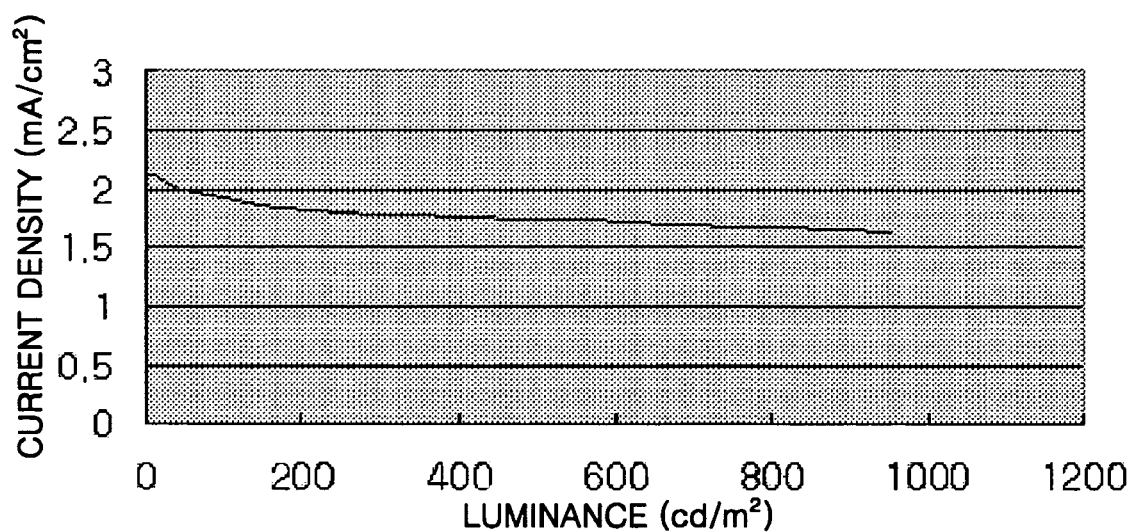

As shown in FIG. 6, the peak light intensity of the first compound (19) was observed at a wavelength of about 441 nm. Color purity corresponded to the CIE color coordinate of x=0.144, y=0.127 in the NTSC chromaticity diagram.

EXAMPLE 2

Manufacture of Organic EL Device

An organic El device was manufactured in the same manner as in Example 1, except that a second compound (33) was used instead of the first compound (19).

Emission characteristics and color purity of the organic EL device according to Example 2 were identified. The results are shown in FIGS. 7-10.

As shown in FIGS. 7-10, when the organic EL device according to Example 2 was provided with a direct current of 7.5 V (the current density was 6.9 mA/cm$^2$), it exhibited an emission luminance of 131 cd/m$^2$, an emission efficiency of 1.9 cd/A, and a color coordinate of (0.169, 0.208). A blue emission with high color purity was attained.

In addition, 0.02 mM of the second compound (33) was prepared by diluting in CH$_2$Cl$_2$. The PL spectrum of the diluted solution was identified by radiating 370 nm UV. The results are shown in FIG. 11.

Figure 11:
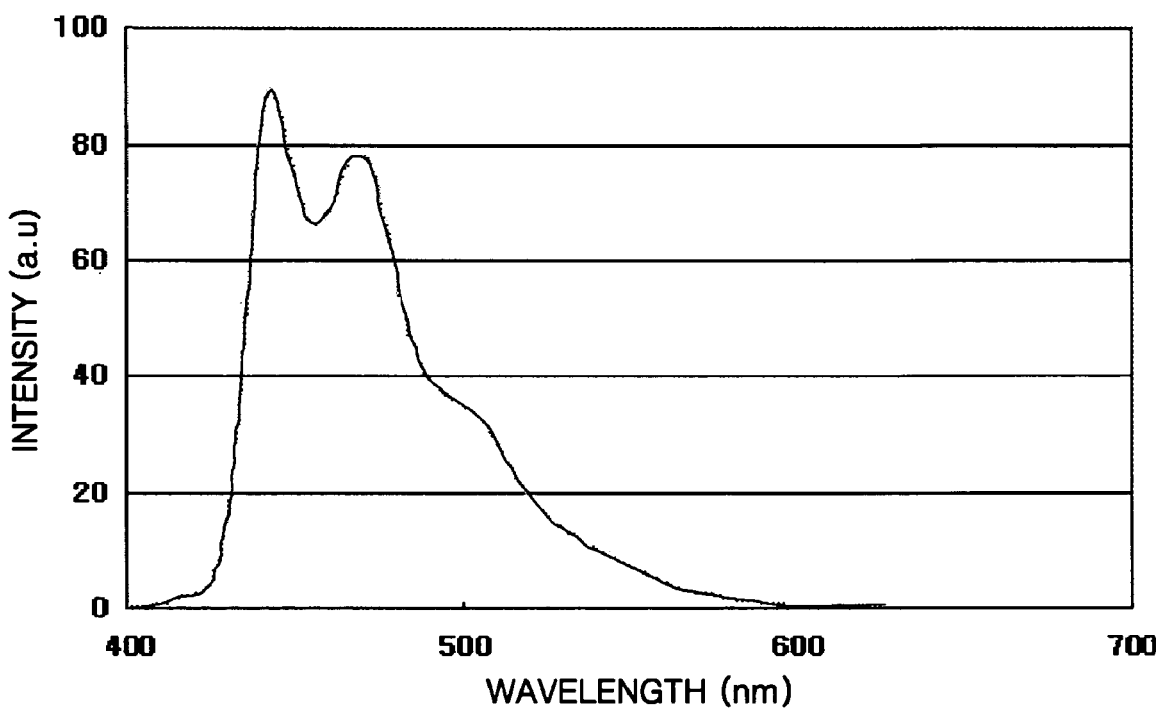
Figure 12:
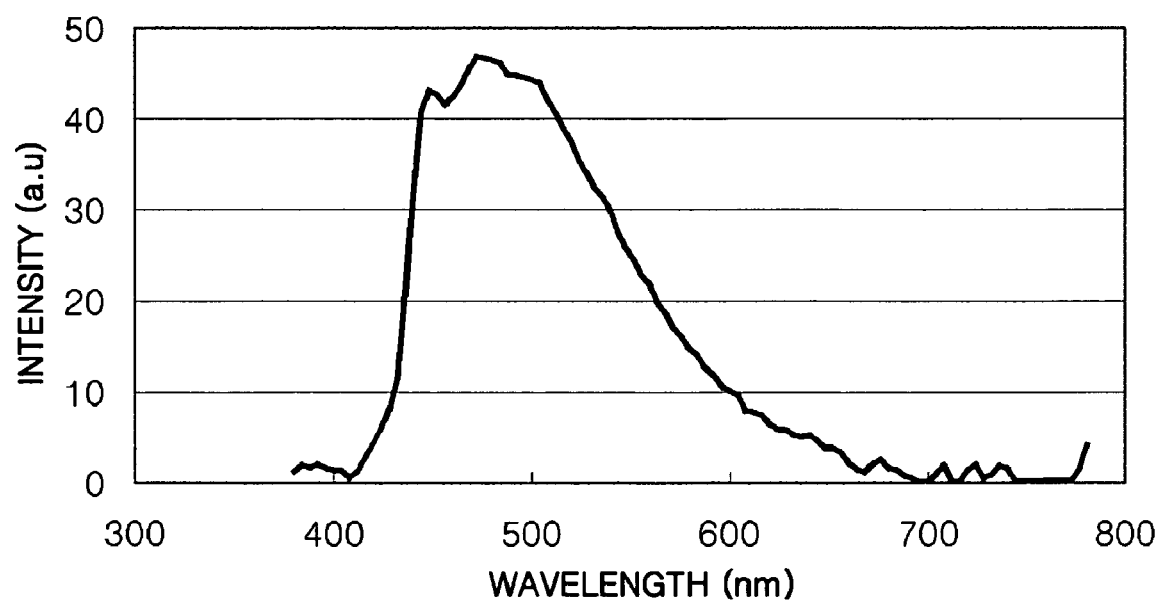
Figure 13:
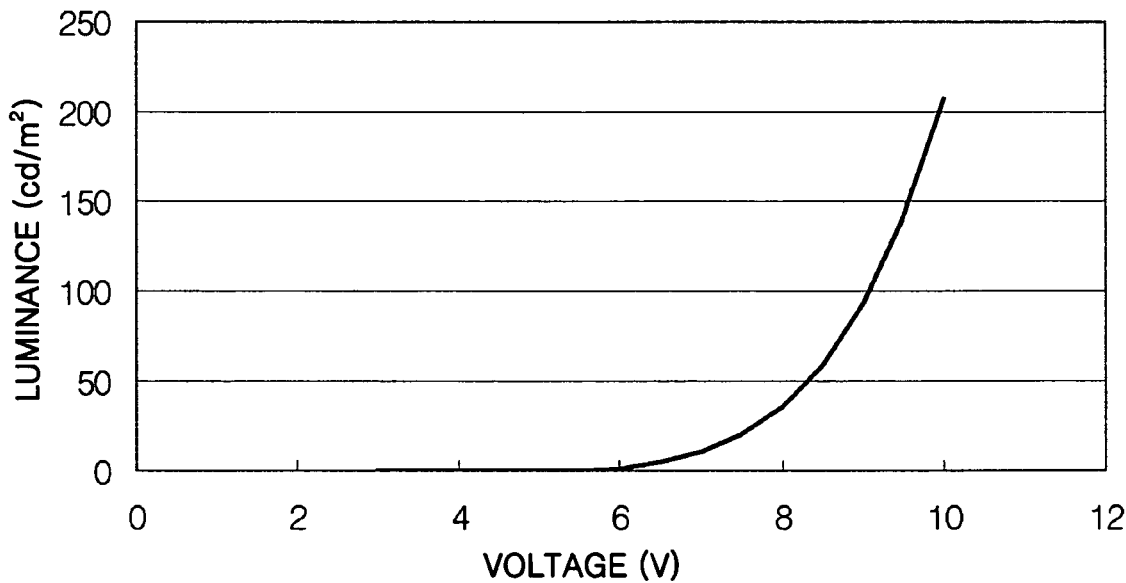
Figure 14:
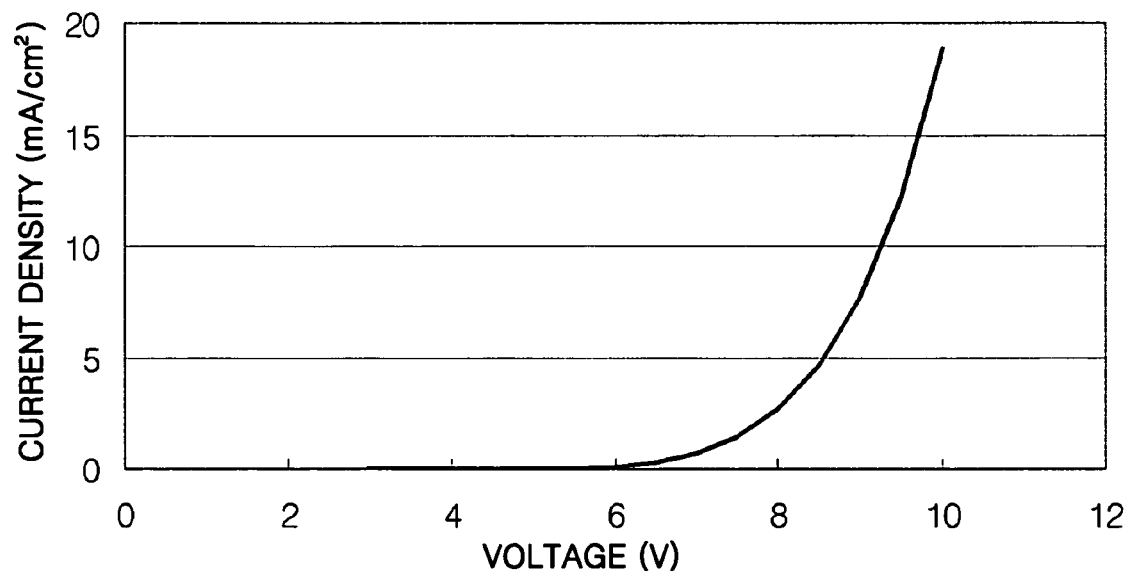
Figure 15:
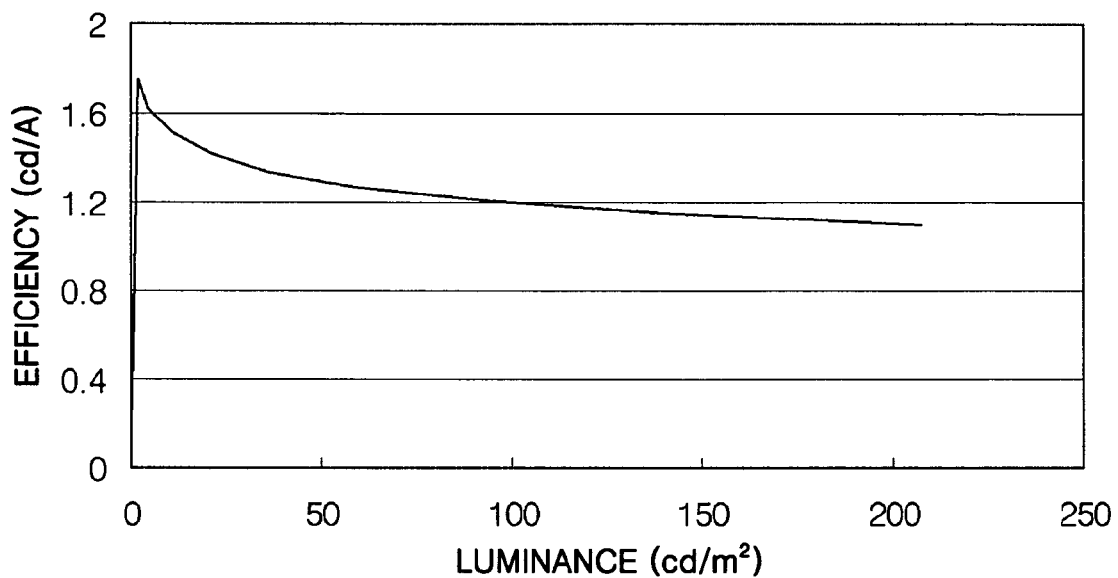

As shown in FIG. 11, the peak light intensity of the second compound (33) was observed at a wavelength of about 443 nm. Color purity corresponded to the CIE color coordinate of x=0.144, y=0.135 in the NTSC chromaticity diagram.

EXAMPLE 3

Manufacture of Organic EL Device

An organic El device was manufactured in the same manner as in Example 1, except that a third compound (136) with a meridional structure was used instead of the first compound (19).

Emission characteristics and color purity of the organic EL device according to Example 3 were identified. The results are shown in FIGS. 12-15.

As shown in FIGS. 12-15, when the organic EL device according to Example 3 was provided with a direct current of 9.5 V (the current density was 12.2 mA/cm$^2$), it exhibited an emission luminance of 140 cd/m$^2$, an emission efficiency of 1.1 cd/A, and a color coordinate of (0.214, 0.301). A blue emission with high color purity was attained.

In addition, 0.02 mM of the third compound (136) with a meridional structure was prepared by diluting in CH$_2$Cl$_2$. The PL spectrum of the diluted solution was identified by radiating 370 nm UV. The results are shown in FIG. 16.

Figure 16:
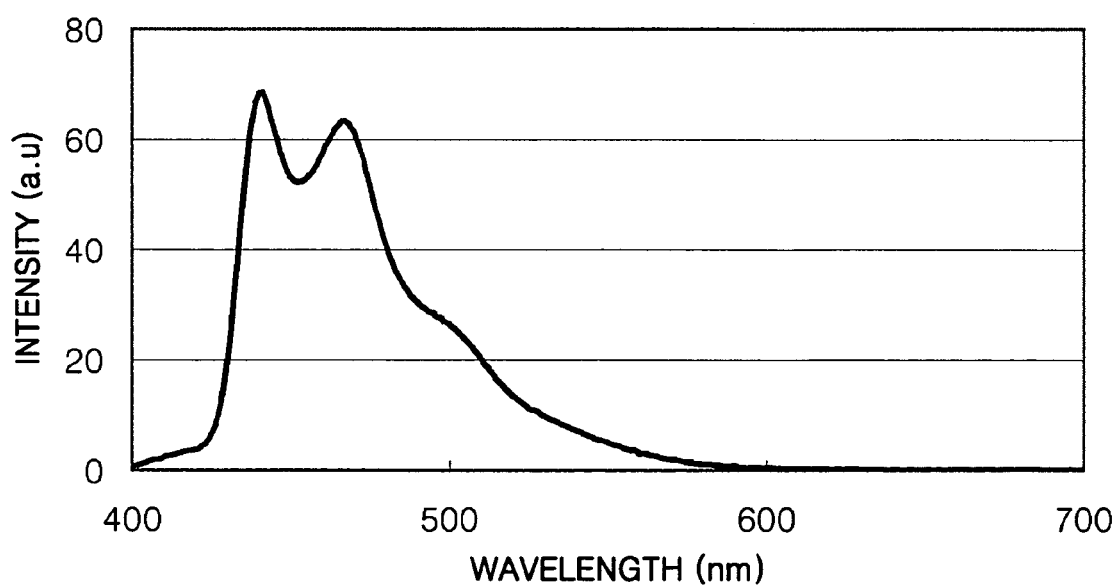
Figure 17:
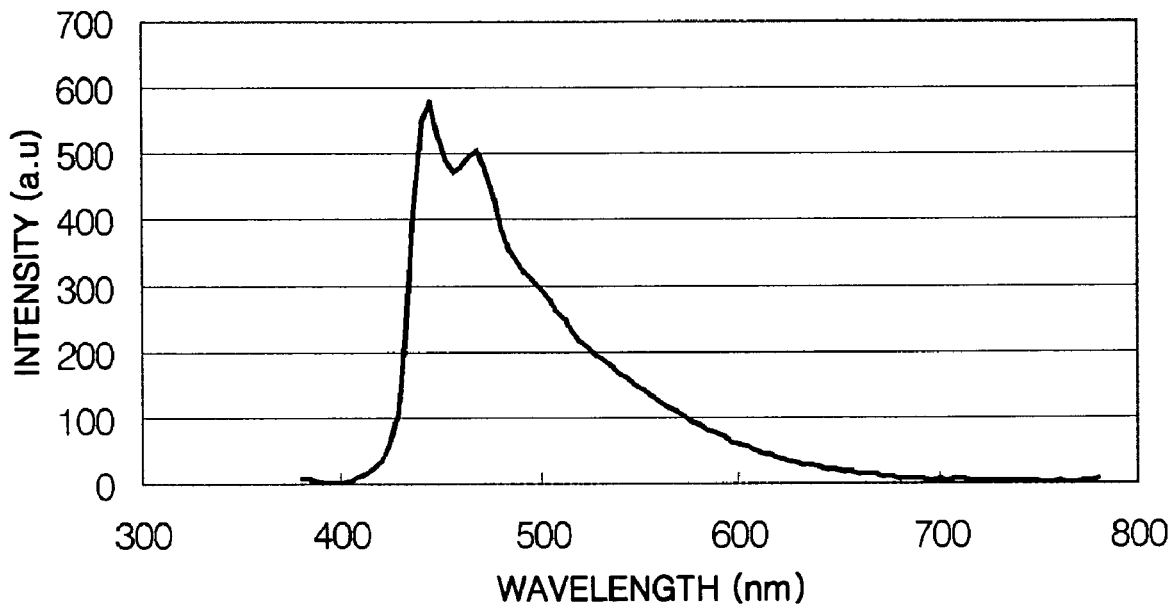
Figure 18:
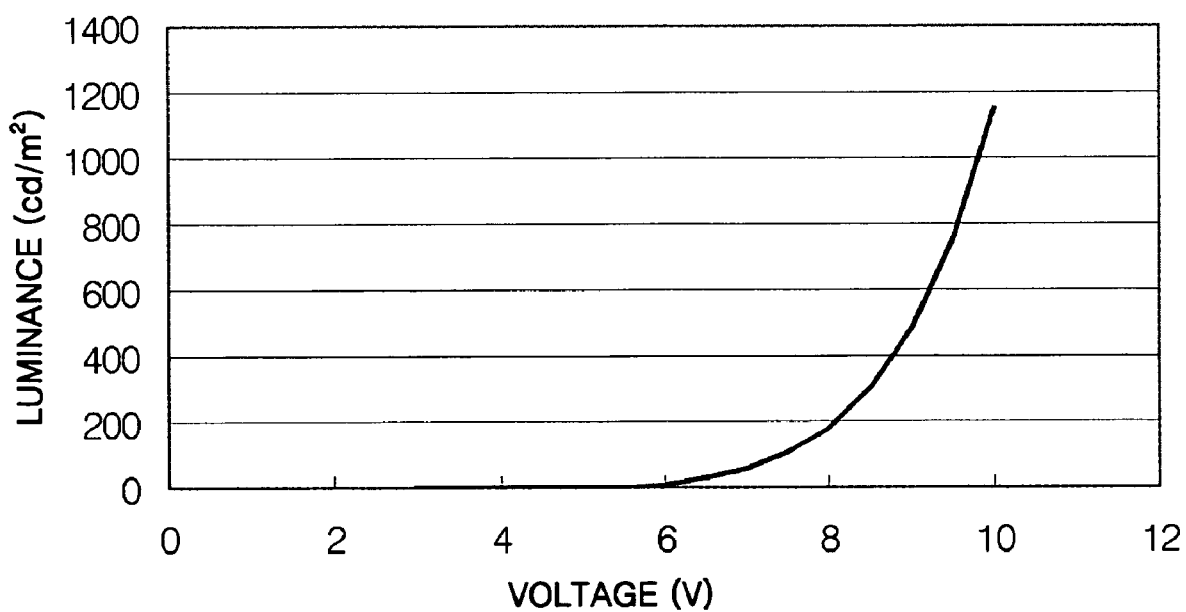
Figure 19:
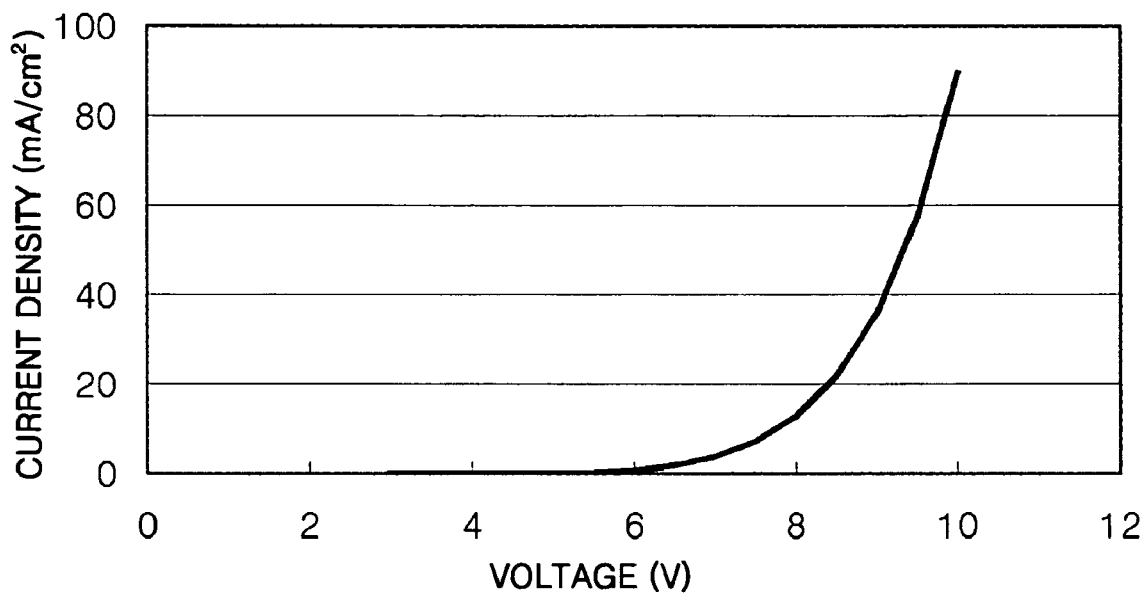
Figure 20:
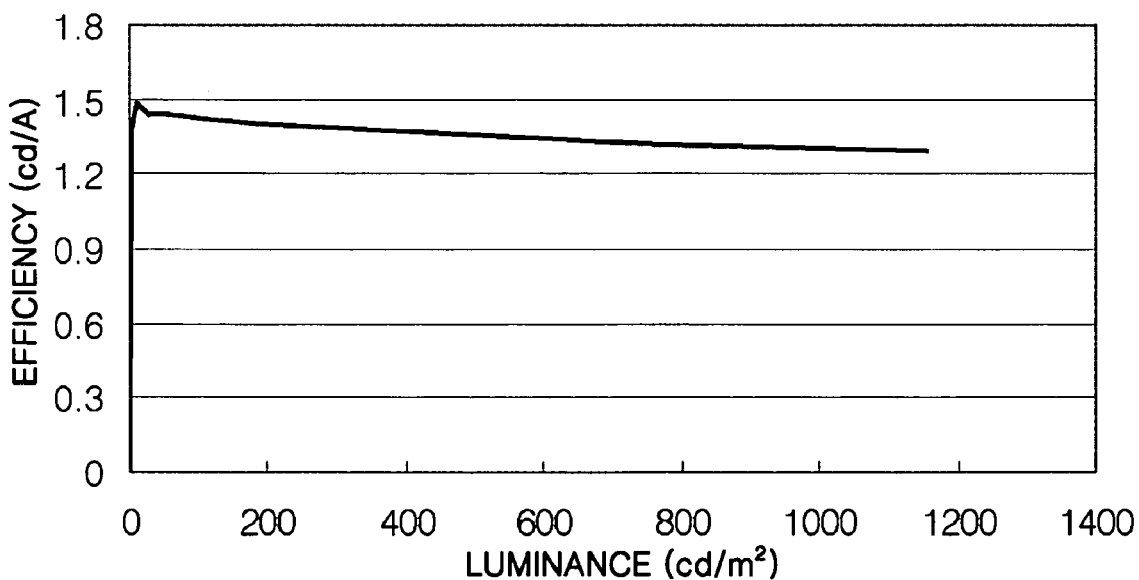

As shown in FIG. 16, the peak light intensity of the third compound (136) was observed at a wavelength of about 441 nm. Color purity corresponded to the CIE color coordinate of x=0.145, y=0.124 in the NTSC chromaticity diagram.

EXAMPLE 4

Manufacture of Organic EL Device

An organic El device was manufactured in the same manner as in Example 1, except that a third compound (136) with a facial structure was used instead of the first compound (19).

Emission characteristics and color purity of the organic EL device according to Example 3 were identified. The results are shown in FIGS. 17-20.

As shown in FIGS. 17-20, when the organic EL device according to Example 4 was provided with a direct current of 7.5 V (the current density was 7.3 mA/cm2), it exhibited an emission luminance of 104 cd/m2, an emission efficiency of 1.4 cd/A, and a color coordinate of (0.193, 0.216). That is, a blue emission with high color purity was attained.

Figure 21:
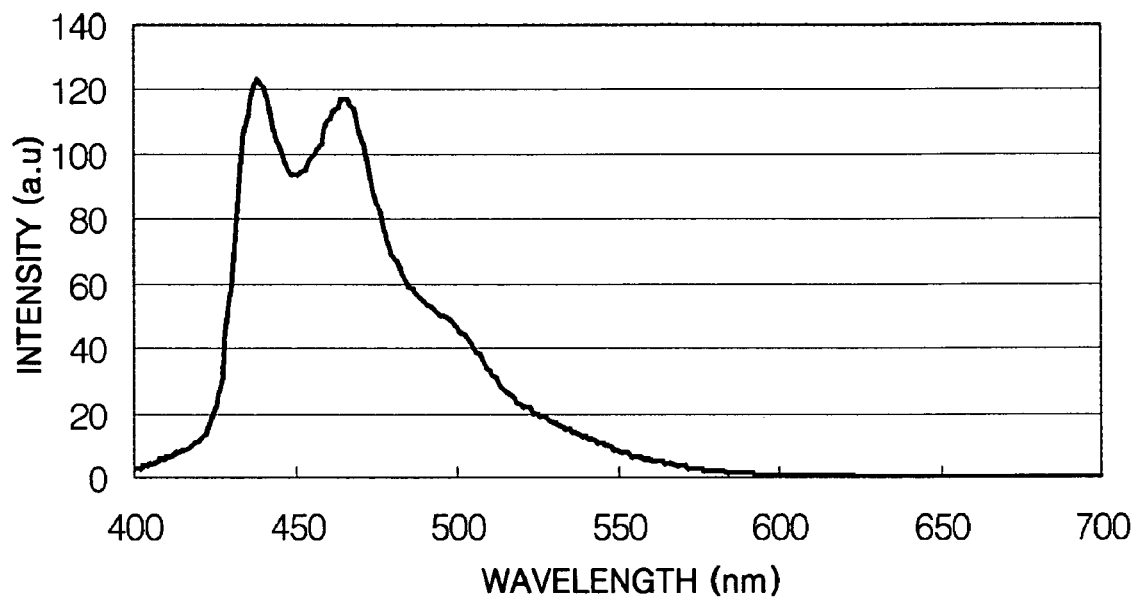

As shown in FIG. 21, the peak light intensity of the third compound (136) with a facial structure was observed at a wavelength of about 438 nm. Color purity corresponded to the CIE color coordinate of x=0.146, y=0.115 in the NTSC chromaticity diagram.

EXAMPLE 5

PL Spectrum Result

A 0.02 mM solution of the fourth compound (138) with a meridional structure in $CH_2Cl_2$ was prepared. The PL spectrum of the diluted solution was identified by radiating 370 nm UV. The results are shown in FIG. 22.

Figure 22:
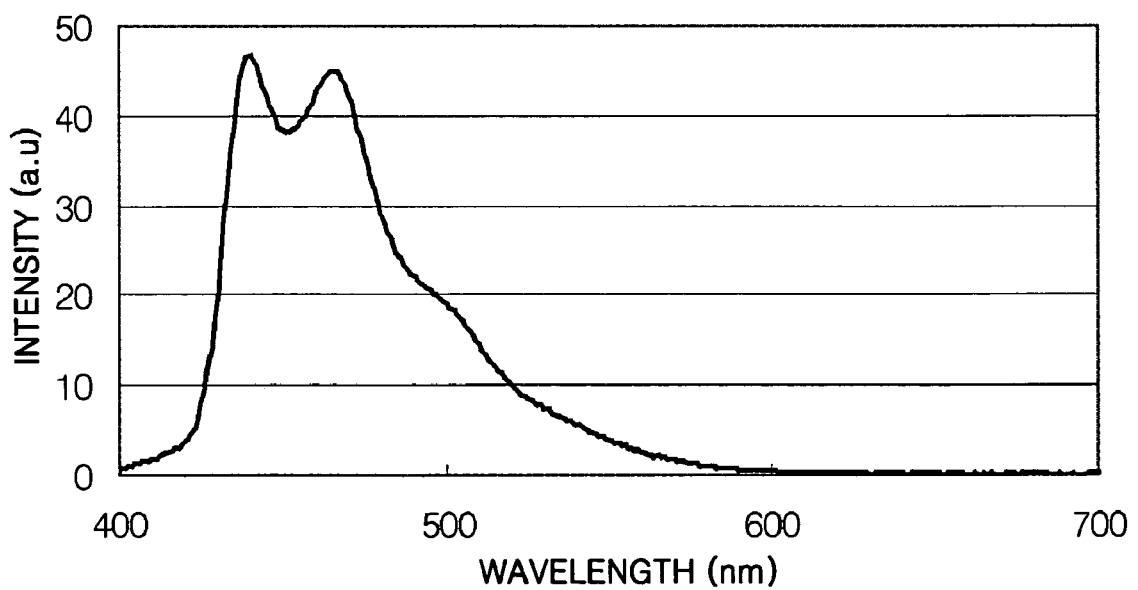

As shown in FIG. 22, the peak light intensity of the fourth compound (138) with a meridional structure was observed at a wavelength of about 440 nm. Color purity corresponded to the CIE color coordinate of x=0.147, y=0.125 in the NTSC chromaticity diagram.

EXAMPLE 6

PL Spectrum Result

A 0.02 mM solution of the fourth compound (138) with a facial structure in $CH_2Cl_2$ was prepared. The PL spectrum of the diluted solution was identified by radiating 370 nm UV. The results are shown in FIG. 23.

Figure 23:
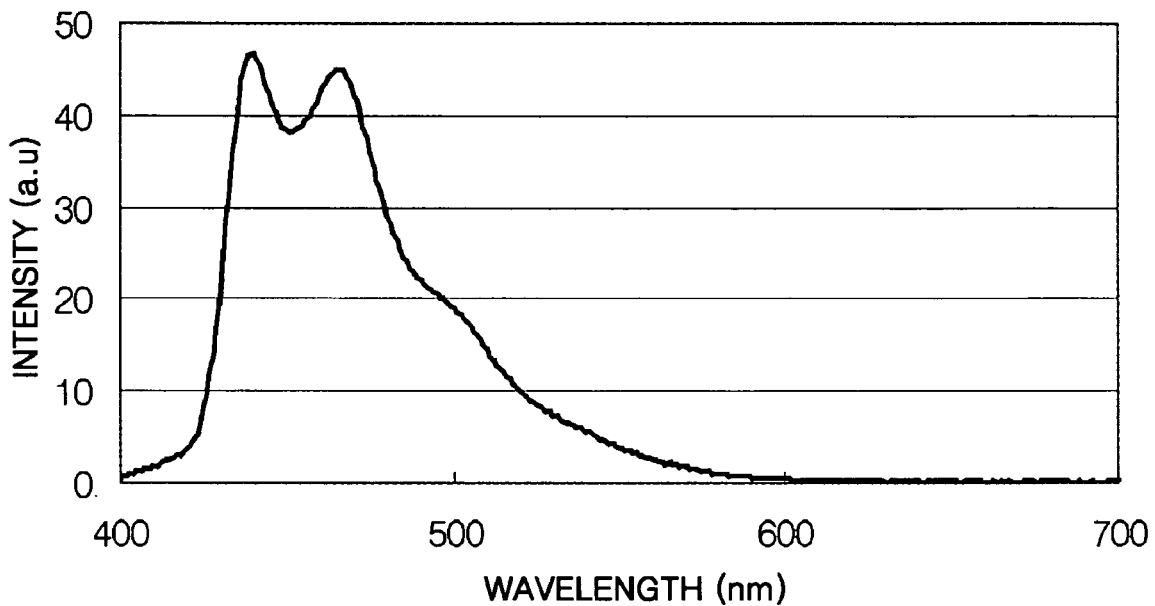

As shown in FIG. 23, the peak intensity light of the fourth compound (138) with a meridional structure was greatest at a wavelength of 440 nm. Color purity corresponded to the CIE (x,y) color coordinate of x=0.146, y=0.122 in the NTSC chromaticity diagram.

EXAMPLE 7

PL Spectrum Result

A 0.02 mM solution of the fifth compound (142) with a meridional structure in $CH_2Cl_2$ was prepared. The PL spectrum of the diluted solution was identified by radiating 370 nm UV. The results are shown in FIG. 24.

Figure 24:
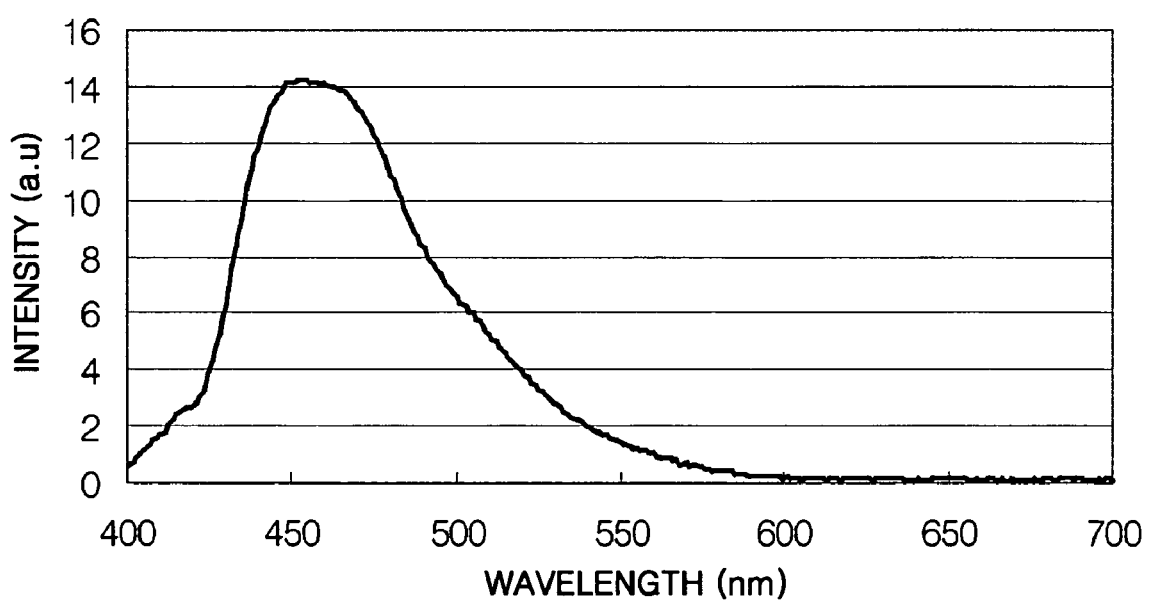

As shown in FIG. 24, the peak light intensity of the fifth compound (142) with a meridional structure was observed at a wavelength of about 448 nm. Color purity corresponded to the CIE color coordinate of x=0.148, y=0.138 In the NTSC chromaticity diagram.

As has been shown, an Ir compound represented by formula 1 may be suitable as a blue phosphorescent material due to its high color purity and excellent emission characteristics. When its light emitting layer is composed of the Ir compound as a dopant and a conventional phosphorescent host, an organic EL device including the light emitting layer may exhibit high luminance, high efficiency, low driving voltage, high color purity, and long lifetime.

While the present invention has been particularly shown and described with reference to exemplary embodiments thereof, various changes may be made without departing from the scope of the present invention.

What is claimed is:

1. An Ir compound represented by formula 2:

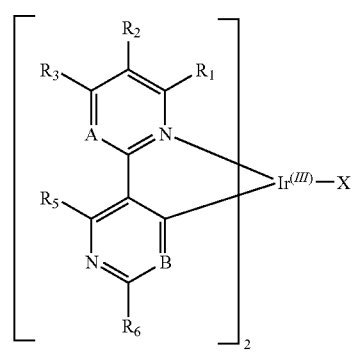

[Formula 2]

wherein A is —CH;

B is —CH;

wherein $R_1$ and $R_2$ are H;

$R_3$ is H, or an electron donating group selected from the group consisting of a methyl group, a methoxy group, an isopropyl group, a phenyloxy group, a benzyloxy group, a dimethylamino group, a diphenylamino group, a pyrrolidine group, and a phenyl group;

$R_5$ and $R_6$ are F; and

X is selected from the group consisting of acetylacetonate (acac), hexafluoroacetylacetonate (hfacac), picolinate (pic), salicylanilide (sal), quinoline carboxylate (quin), 8-hydroxyquinolinate (hquin), L-proline (L-pro), 1,5-dimethyl-3-pyrazolecarboxylate (dm3pc), imineacetylacetonate (imineacac), dibenzoylmethane (dbm), tetrametyl heptandionate (tmd), 1-(2-hydroxyphenyl) pyrazolate (oppz), and phenylpyrazole (ppz).

2. The Ir compound of claim 1, wherein the compound is selected from the group consisting of compounds represented by the following formulas:

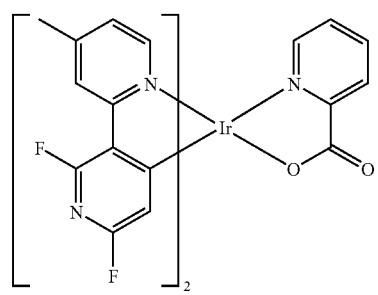

(19)

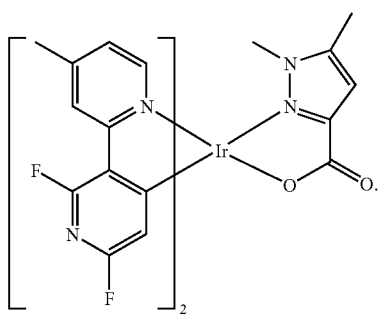

(33)

3. A compound represented by formula 3:

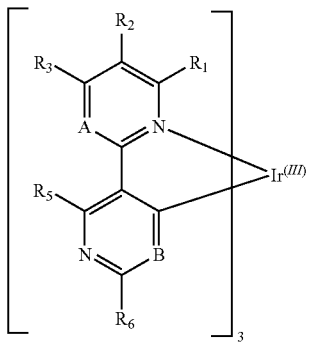

wherein A is —CH;

B is —CH;

$R_1$ and $R_2$ are H;

$R_3$ is H, or an electron donating group selected from the group consisting of a methyl group, a methoxy group, an isopropyl group, a phenyloxy group, a benzyloxy group, a dimethylamino group, a diphenylamino group, a pyrrolidine group, and a phenyl group; and $R_5$ and $R_6$ are F.

4. The Ir compound of claim 3, wherein the compound is selected from the group consisting of compounds represented by the following formulas:

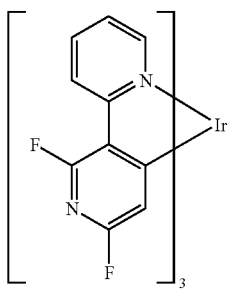
(136)

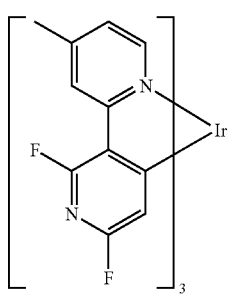
(138)

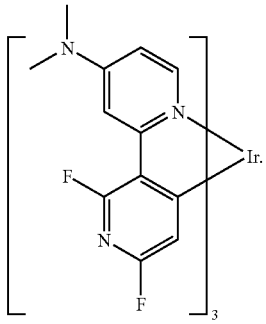
(142)

5. An organic electroluminescent device comprising an organic film interposed between a pair of electrodes, the organic film comprising an Ir compound represented by formula 2:

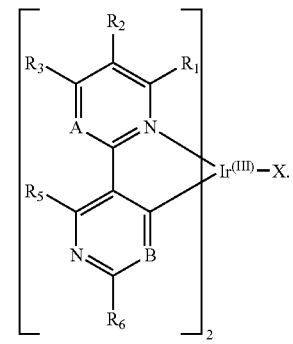

wherein A is —CH;

B is —CH;

$R_1$ and $R_2$ are H;

$R_3$ is H, or an electron donating group selected from the group consisting of a methyl group, a methoxy group, an isopropyl group, a phenyloxy group, a benzyloxy group, a dimethylamino group, a diphenylamino group, a pyrrolidine group, and a phenyl group;

$R_5$ and $R_6$ are F; and

X is selected from the group consisting of acetylacetonate (acac), hexafluoroacetylacetonate (hfacac), picolinate (pic), salicylanilide (sal), quinoline carboxylate (quin), 8-hydroxyquinolinate (hquin), L-proline (L-pro), 1,5-dimethyl-3-pyrazolecarboxylate (dm3pc), imineacetylacetonate (imineacac), dibenzoylmethane (dbm), tetrametyl heptandionate (tmd), 1-(2-hydoxyphenyl) pyrazolate (oppz), and phenylpyrazole (ppz).

6. The organic electroluminescent device of claim 5, wherein the organic film is a light emitting layer.

7. The organic electroluminescent device of claim 6, wherein the light emitting layer comprises 1-20 parts by weight of the Ir compound as a dopant based on 100 parts by weight of a host and a dopant.

8. An organic electroluminescent device comprising an organic film interposed between a pair of electrodes, the organic film comprising an Ir compound represented by formula 3:

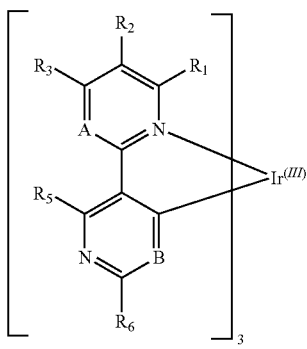

wherein A is —CH;
B is —CH;
wherein $R_1$ and $R_2$ all are H;
$R_3$ is H, or an electron donating group selected from the group consisting of a methyl group, a methoxy group, an isopropyl group, a phenyloxy group, a benzyloxy group, a dimethylamino group, a diphenylamino group, a pyrrolidine group, and a phenyl group; and
$R_5$ and $R_6$ are F.

9. The organic electroluminescent device of claim 8, wherein the organic film is a light emitting layer.

10. The organic electroluminescent device of claim 9, wherein the light emitting layer comprises 1-20 parts by weight of the Ir compound as a dopant based on 100 parts by weight of a host and a dopant.

* * * * *

UNITED STATES PATENT AND TRADEMARK OFFICE
CERTIFICATE OF CORRECTION

PATENT NO. : 7,585,573 B2 Page 1 of 1
APPLICATION NO. : 11/046758
DATED : September 8, 2009
INVENTOR(S) : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1046 days.

Signed and Sealed this

Fourteenth Day of September, 2010

David J. Kappos
*Director of the United States Patent and Trademark Office*